United States Patent
Zhao et al.

(10) Patent No.: US 12,396,364 B2
(45) Date of Patent: Aug. 19, 2025

(54) NITROGEN-CONTAINING ORGANIC COMPOUND, USE THEREOF, AND ORGANIC ELECTROLUMINESCENT DEVICE USING SAME

(71) Applicant: Shaanxi Lighte Optoelectronics Material Co., Ltd., Xi'an (CN)

(72) Inventors: Yu Zhao, Xi'an (CN); Zhen Xue, Xi'an (CN); Jinping Wang, Xi'an (CN)

(73) Assignee: Shaanxi Lighte Optoelectronics Material Co., Ltd., Xi'an (CN)

( * ) Notice: Subject to any disclaimer, the term of this patent is extended or adjusted under 35 U.S.C. 154(b) by 901 days.

(21) Appl. No.: 17/620,262

(22) PCT Filed: Dec. 24, 2020

(86) PCT No.: PCT/CN2020/138932
§ 371 (c)(1),
(2) Date: Dec. 17, 2021

(87) PCT Pub. No.: WO2021/136055
PCT Pub. Date: Jul. 8, 2021

(65) Prior Publication Data
US 2022/0302391 A1    Sep. 22, 2022

(30) Foreign Application Priority Data
Dec. 30, 2019  (CN) .......................... 201911398125.3

(51) Int. Cl.
*H10K 85/60* (2023.01)
*C07D 471/04* (2006.01)
*C09K 11/06* (2006.01)
*H10K 50/16* (2023.01)

(52) U.S. Cl.
CPC ....... *H10K 85/6572* (2023.02); *C07D 471/04* (2013.01); *C09K 11/06* (2013.01); *H10K 85/6574* (2023.02); *H10K 85/6576* (2023.02); *C09K 2211/1011* (2013.01); *C09K 2211/1059* (2013.01); *H10K 50/16* (2023.02); *H10K 85/654* (2023.02)

(58) Field of Classification Search
CPC ............. C07D 471/04; H10K 85/6572; H10K 85/6574; H10K 85/6576; H10K 85/654; H10K 50/16; C09K 11/06; C09K 2211/1011; C09K 2211/1059
See application file for complete search history.

(56) References Cited

U.S. PATENT DOCUMENTS

| | | | |
|---|---|---|---|
| 11,450,818 B2* | 9/2022 | Zhang | H10K 85/615 |
| 2014/0077191 A1* | 3/2014 | Mizutani | H10K 85/6574 546/88 |
| 2016/0248024 A1* | 8/2016 | Shin | H10K 85/6574 |

FOREIGN PATENT DOCUMENTS

WO    WO-2014178532 A1 * 11/2014    ........... C07D 401/04

OTHER PUBLICATIONS

Park et al., machine translation of WO-2014178532-A1 (2014) pp. 1-59. (Year: 2014).*

* cited by examiner

*Primary Examiner* — Dylan C Kershner
(74) *Attorney, Agent, or Firm* — Tucker Ellis LLP

(57) ABSTRACT

Provided are a nitrogen-containing organic compound, the use thereof, and an organic electroluminescent device using same. The nitrogen-containing organic compound has a chemical structure with pyridoquinazoline as the center, wherein one side is connected with an aryl-containing group, the other side is connected with other aryl groups having an electron transport performance, thereby forming a small molecule OLED material with an asymmetric structure, which has a good film-forming property. The molecule contains large rigid groups, and has a high thermal stability. When the nitrogen-containing organic compound is applied in OLED devices as an electron transport material, good device performances and a low voltage can be achieved.

5 Claims, 1 Drawing Sheet

NITROGEN-CONTAINING ORGANIC COMPOUND, USE THEREOF, AND ORGANIC ELECTROLUMINESCENT DEVICE USING SAME

CROSS REFERENCE TO RELATED APPLICATIONS

The present application claims priority to Chinese patent application No. CN201911398125.3 filed on Dec. 30, 2019, and the full content of the above Chinese patent application is incorporated herein as a part of the present application.

TECHNICAL FIELD

The present disclosure relates to the field of organic light-emitting material, and specifically provides a nitrogen-containing organic compound, the use thereof, and an organic electroluminescent device using same.

BACKGROUND

The principle of an organic light-emitting diode (OLED) is that when an electric field is applied to a cathode and an anode, holes at the anode side and electrons at the cathode side will move to a light-emitting layer where the holes and electrons are combined to form excitons which release energy outward in an excited state, and light is emitted to the outside in the process of changing from an excited state with energy released to a ground state.

Since molecular-scale organic electroluminescence was reported by Kodak in 1987 and polymer electroluminescence was reported by University of Cambridge in 1990, research and development have been carried out one after another by all countries in the world. This material has the advantages of simple structure, high yield, low cost, active luminescence, fast response, high fraction and the like, and has the properties of low driving voltage, all-solid state, non-vacuum, anti-oscillation, low temperature (−40° C.) resistance and the like, and it is considered to be a new technique most likely to replace liquid crystal display in the future, and has attracted great attention.

In order to improve the luminance, efficiency and lifetime of the organic electroluminescent device, multilayer structures are usually used in organic electroluminescent devices, and these multilayer structures may include one or more of the film layers as follows: hole injection layer (HIL), hole transport layer (HTL), electron-blocking layer (EBL), emitting layer (EML), hole-blocking layer (HBL), electron transport layer (ETL), electron injection layer (EIL) and the like. These film layers can improve the injection efficiency of carriers (holes and electrons) at the interfaces among layers and balance the transport capability of carriers between layers, thus improving the luminance and efficiency of the organic electroluminescent device.

In organic electroluminescent devices, the existing hole transport materials, such as NPB, TPD, m-MTDATA and other materials, generally have low luminous efficiency and poor thermal stability, resulting in short lifetime and low luminous efficiency of organic electroluminescent devices.

SUMMARY

The present disclosure is intended to provide an organic electroluminescent material with an excellent performance, which can be used as an electron transport layer in an organic electroluminescent device.

In order to achieve the above purpose, a first aspect of the present disclosure provides a nitrogen-containing organic compound having a structure represented by formula (1):

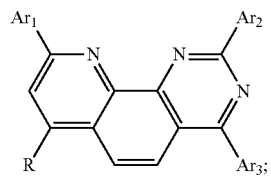

Formula (1)

wherein R is hydrogen or deuterium;

$Ar_1$, $Ar_2$ and $Ar_3$ are the same or different, and are each independently selected from a group consisting of the following groups: a substituted or unsubstituted aryl with 6 to 60 carbon atoms, a substituted or unsubstituted heteroaryl with 2 to 60 carbon atoms, and a substituted or unsubstituted aralkyl with 6 to 30 carbon atoms;

the substituents of $Ar_1$, $Ar_2$ and $Ar_3$ are the same or different, and are each independently selected from a group consisting of the following groups: deuterium, a halogen, a cyano, an alkyl with 1 to 10 carbon atoms, a cycloalkyl with 3 to 10 carbon atoms, a heterocycloalkyl with 2 to 10 carbon atoms, a substituted or unsubstituted aryl with 6 to 30 carbon atoms, a substituted or unsubstituted heteroaryl with 3 to 30 carbon atoms, an alkoxyl with 1 to 30 carbon atoms and an alkylsilyl with 1 to 30 carbon atoms.

A second aspect of the present disclosure provides a use of the nitrogen-containing organic compound described in the first aspect of the present disclosure in an organic electroluminescent device.

A third aspect of the present disclosure provides an organic electroluminescent device, comprising an anode, a cathode, and at least a functional layer between the anode and the cathode, wherein the functional layer comprises a hole injection layer, a hole transport layer, an organic electroluminescent layer, an electron transport layer and an electron injection layer, and the electron transport layer contains the nitrogen-containing organic compound according to the first aspect of the present disclosure.

The nitrogen-containing compound of the present disclosure is a derivative with pyridoquinazoline as a parent nucleus, which has a strong electron donating performance and contains an aryl substituent group to form a large conjugated system, which is beneficial to electron migration and transport. The nitrogen-containing organic compound of the present disclosure has a high thermal stability, and can improve the luminous efficiency of the organic electroluminescent device, reduce the driving voltage and prolong the lifetime of the devices when used as an electron transport layer material of the organic electroluminescent device.

A detailed description of other characteristics and advantages of the present disclosure will be described in the DETAILED DESCRIPTION OF THE EMBODIMENTS below.

BRIEF DESCRIPTION OF THE DRAWINGS

The drawings are intended to provide a further understanding of the present disclosure and form a part of the specification. They are used for interpreting the present disclosure together with the DETAILED DESCRIPTION OF THE EMBODIMENTS below, but do not constitute a limitation to the present disclosure. In the drawings.

Figure 1:
FIG. 1 illustrates a structural view of an embodiment of the organic electroluminescent device of the present disclosure.
Figure 2:
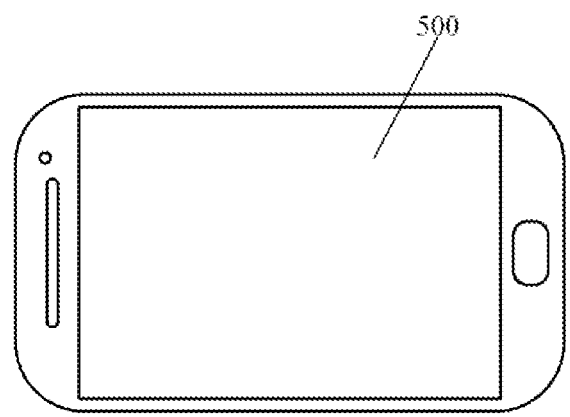
FIG. 2 illustrates a schematic view of an embodiment of the organic electroluminescent device of the present disclosure used for electronic device.

The reference numerals of main elements in the drawings are described as follows:

100. Anode; 200. Cathode; 300. Functional layer; 310. Hole injection layer; 320. Hole transport layer; 321. First hole transport layer; 322. Second hole transport layer; 330. Organic electroluminescent layer; 340. Hole-blocking layer; 350. Electron transport layer; 360. Electron injection layer; 370. Electron-blocking layer; 500. Electronic device.

DETAILED DESCRIPTION OF THE EMBODIMENTS

The embodiments of the present disclosure will be described in detail below in combination with the drawings. It should be understood that the embodiments described here are only for illustration and explanation of the present disclosure, not used to limit the present disclosure.

A first aspect of the present disclosure provides a nitrogen-containing organic compound having a structure represented by formula (1):

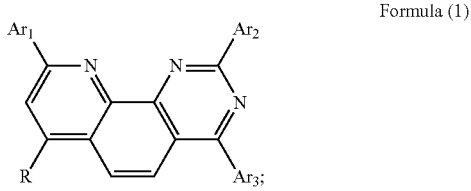

Formula (1)

wherein R is hydrogen or deuterium;

$Ar_1$, $Ar_2$ and $Ar_3$ are the same or different, and are each independently selected from a group consisting of the following groups: a substituted or unsubstituted aryl with 6 to 60 carbon atoms, a substituted or unsubstituted heteroaryl with 2 to 60 carbon atoms, and a substituted or unsubstituted aralkyl with 6 to 30 carbon atoms;

the substituents of $Ar_1$, $Ar_2$ and $Ar_3$ are the same or different, and are each independently selected from a group consisting of the following groups: deuterium, a halogen, a cyano, an alkyl with 1 to 10 carbon atoms, a cycloalkyl with 3 to 10 carbon atoms, a heterocycloalkyl with 2 to 10 carbon atoms, a substituted or unsubstituted aryl with 6 to 30 carbon atoms, a substituted or unsubstituted heteroaryl with 3 to 30 carbon atoms, an alkoxyl with 1 to 30 carbon atoms and an alkylsilyl with 1 to 30 carbon atoms.

The nitrogen-containing organic compound of the present disclosure has a chemical structure with pyridoquinazoline as the center, wherein a side is connected with an aryl-containing group, another side is connected with other aryl groups having an electron transport performance, thereby forming a small molecule OLED material with an asymmetric structure, which has a good film-forming property. The molecule contains large rigid groups, and has a high thermal stability. When the nitrogen-containing organic compound is applied in OLED devices as an electron transport material, good device performances and a low voltage can be achieved.

In the present disclosure, as a way of description in use, "each . . . is independently"is interchangeable with" . . . are respectively independently"and" . . . is independently selected from", all of which shall be understood in a broad sense; it can mean that the specific options expressed between the same symbols in different groups do not affect each other, and can also indicate that the specific options expressed between the same symbols in the same group do not affect each other. For example,

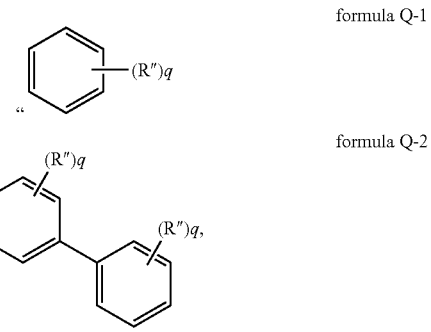

formula Q-1 formula Q-2 wherein each q is independently 0, 1, 2 or 3, and each R" is independently selected from hydrogen, deuterium, fluorine or chlorine", means that: formula Q-1 indicates that there are q substituents R" on a benzene ring, each R" may be the same or different, and the options of each R" do not affect each other; formula Q-2 indicates that there are q substituents R" on each benzene ring of biphenyl, the number q of R" substituents of the two benzene rings may be the same or different, R" may be the same or different, and the options of each R" do not affect each other.

In the present disclosure, the term "a substituted or unsubstituted" refers to no substituent or being substituted by one or more substituents. The substituents include, but are not limited to, deuterium, halogen groups (F, Cl, Br), cyano, alkyl, alkenyl, alkynyl, haloalkyl, aryl, heteroaryl, aryloxy, arylthio, silyl, alkylamine, cycloalkyl or heterocyclyl.

In the present disclosure, an alkyl with 1 to 10 carbon atoms is either a linear alkyl or a branched alkyl. Specifically, an alkyl with 1 to 10 carbon atoms is either a linear alkyl with 1 to 10 carbon atoms, or a branched alkyl with 3 to 10 carbon atoms; further, it is either a linear alkyl with 1 to 10 carbon atoms, or a branched alkyl with 3 to 10 carbon atoms. More specifically, an alkyl with 1 to 10 carbon atoms may be, but is not limited to, methyl, ethyl, n-propyl, isopropyl, n-butyl, isobutyl, tert-butyl, n-pentyl, isopentyl, neopentyl, cyclopentyl, hexyl, cyclohexyl, heptyl, octyl, 2-ethylhexyl, nonyl, decyl, 3,7-dimethyloctyl and the like.

In the present disclosure, the aryl refers to an optional functional group or substituent derived from an aromatic hydrocarbon ring. The aryl may be a monocyclic aryl or a polycyclic aryl, in other words, the aryl may be a monocyclic aryl, a fused ring aryl, two or more monocyclic aryls conjugated by carbon-carbon bonds, a monocyclic aryl and a fused ring aryl conjugated by carbon-carbon bonds, and two or more fused ring aryls conjugated by carbon-carbon bonds. That is, two or more aromatic groups conjugated by carbon-carbon bonds can also be regarded as the aryl of the present disclosure. Wherein the aryl does not contain heteroatoms such as B, O, N, P, Si, Se or S. Specifically, aryl with 6 to 60 carbon atoms may be monocyclic or polycyclic aryl with 6 to 48 carbon atoms, preferably monocyclic or polycyclic aryl with 6 to 30 carbon atoms; or monocyclic or polycyclic aryl with 6 to 20 carbon atoms. More specifically, aryl with 6 to 60 carbon atoms as monocyclic aryl may be phenyl, biphenyl or triphenyl, tetrabiphenyl, 1,3,5-triphenylphenyl and the like; as polycyclic aryl, it may be one or more of naphthyl, anthracyl, phenanthrenyl, tetracene, triphenylene, pyrenyl, perylenyl, chrysenyl, fluorenyl, naphthylphenyl, anthracylphenyl, phenanthrenylphenyl, triphenylenylphenyl, pyrenylphenyl, perylenylphenyl, chrysenylphenyl, fluorenylphenyl, phenylnaphthyl, phenylphenanthrenyl, phenylanthracyl or phenylnaphthylphenyl. But it is not limited to this.

In the present disclosure, substituted aryl means that one or more hydrogen atoms in the aryl are substituted by other groups. For example, at least one hydrogen atom is substituted by a deuterium atom, F, Cl, Br, I, CN, a hydroxyl, an amino, a branched alkyl, a linear alkyl, a cycloalkyl, an alkoxy, an alkylamine or other groups. It is understood that the substituted aryl with 18 carbon atoms means that the total number of carbon atoms of the aryl and the substituents of the aryl is 18. For example, the number of carbon atoms of 9, 9-dimethylfluorenyl is 15.

Examples of aryls as substituents herein include, but are not limited to phenyl, biphenyl, naphthyl, 9, 9-dimethylfluorenyl, 9, 9-diphenylfluorene, spirodifluorenyl, anthracyl, phenanthryl or chrysenyl.

In the present disclosure, unsubstituted aryl refers to aryl with 6 to 30 carbon atoms, such as: phenyl, naphthyl, pyrenyl, dimethylfluorenyl, 9, 9-diphenylfluorene, spirodifluorenyl, anthracyl, phenanthryl, chrysenyl, azulenyl, acenaphthenyl, biphenyl, benzoanthracenyl, spirodifluorenyl, perylenyl, indenyl and the like. Substituted aryl with 6 to 30 carbon atoms refers to at least one hydrogen atom substituted by a deuterium atom, F, Cl, I, CN, a hydroxyl, a nitro, an amino and the like.

In the present disclosure, the heteroaryl may be a heteroaryl including at least one of B, O, N, P, Si, Se and S as a heteroatom. The heteroaryl may be monocyclic or polycyclic heteroaryl, in other words, the heteroaryl is either a single aromatic ring system or a plurality of aromatic ring systems conjugated by carbon-carbon bonds, and any aromatic ring system is an aromatic monocycle or an aromatic fused ring. Exemplarily, the heteroaryl may include, but is not limited to, thiophenyl, furanyl, pyrrolyl, imidazolyl, thiazolyl, oxazolyl, oxadiazole, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidyl, pyridopyrazinyl, pyrazinopyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothiophenyl, dibenzothiophenyl, thiophenothiophenyl, benzofuranyl, phenanthrolinyl, isoxazolyl, thiadiazolyl, benzothiazolyl, phenothiazinyl, dibenzosilyl, dibenzofuranyl, dibenzofuranyl substituted by phenyl, phenyl substituted by dibenzofuranyl and the like. Wherein thiophenyl, furanyl, phenanthrolinyl and the like are heteroaryls of a single aromatic ring system, and N-arylcarbazolyl, N-heteroarylcarbazolyl, dibenzofuranyl substituted by phenyl, phenyl substituted by dibenzofuranyl and the like are heteroaryls of a plurality of aromatic ring systems conjugated by carbon-carbon bonds.

In the present disclosure, heteroaryls as substituents are for example, but are not limited to pyridyl, pyrimidyl, carbazolyl, dibenzofuranyl or dibenzothiophenyl.

In the present disclosure, the number of carbon atoms of a substituted or unsubstituted aryl may be 6, 7, 8, 9, 10, 12, 14, 15, 16, 18, 20, 21, 22, 24, 25, 26, 27, 30, 32, or 33; the number of carbon atoms of a substituted or unsubstituted heteroaryl may be 3, 4, 5, 12, 18, 22, or 24.

The "rings" herein include saturated rings and unsaturated rings; saturated rings are cycloalkyl and heterocycloalkyl, and unsaturated rings are cycloalkenyl, heterocycloalkenyl, aryl and heteroaryl.

In the present disclosure,

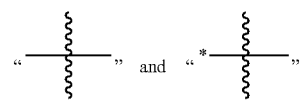

have the same meaning, and both of them refer to the position bound with other substituents or binding sites.

A non-orientating connection bond herein refers to a single bond

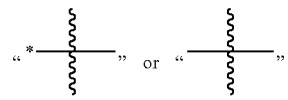

protruding from a ring system, which means that one end of the connection bond can be connected to any position in the ring system penetrated by the bond, and the other end is connected to the rest of a compound molecule. For example, as shown in the following formula (f), the naphthyl represented by formula (f) is connected with other positions of the molecule through two non-orientating connection bonds penetrating double rings, and what it means includes any possible connection mode represented by formula (f-1) ~formula (f-10).

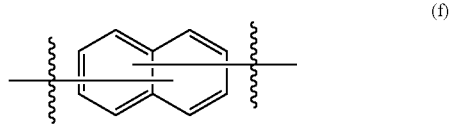

(f)

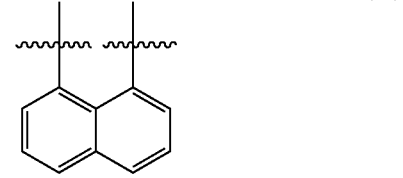

(f-1)

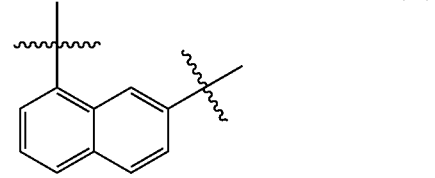

(f-2)

(f-3)
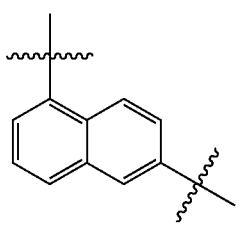
(f-4)
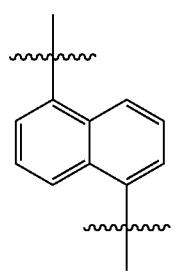
(f-5)
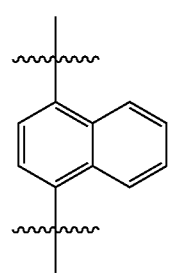
(f-6)
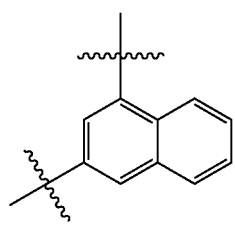
(f-7)
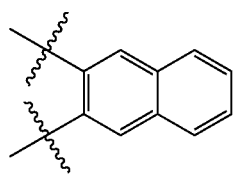
(f-8)
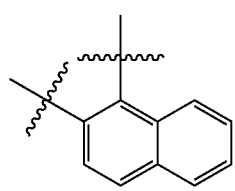
(f-8)
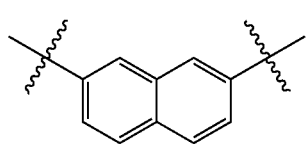
(f-10)
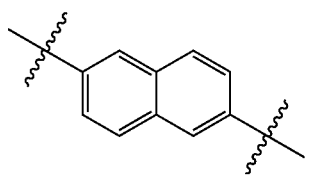
For example, as shown in the following formula (X'), the phenanthryl represented by formula (X') is connected with other positions of the molecule through a non-orientating connection bond protruding from a benzene ring at one side, and what it means includes any possible connection mode represented by formula (X'-1)~formula (X'-4).
(X')
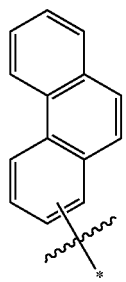
(X'-1)
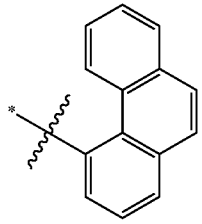
(X'-2)
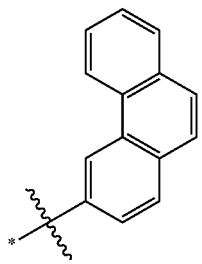
(X'-3)
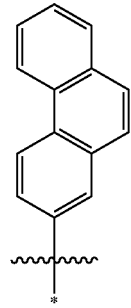

(X'-4)

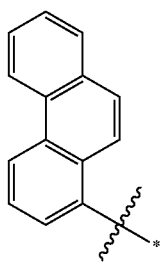

A non-orientating substituent herein refers to a substituent connected by a single bond protruding from the center of a ring system, which means that the substituent can be connected in any possible position in the ring system. For example, as shown in the following formula (Y), the substituent R group represented by formula (Y) is connected with a quinoline ring through a non-orientating connection bond, and what it means includes any possible connection mode represented by formula (Y-1)~formula (Y-7).

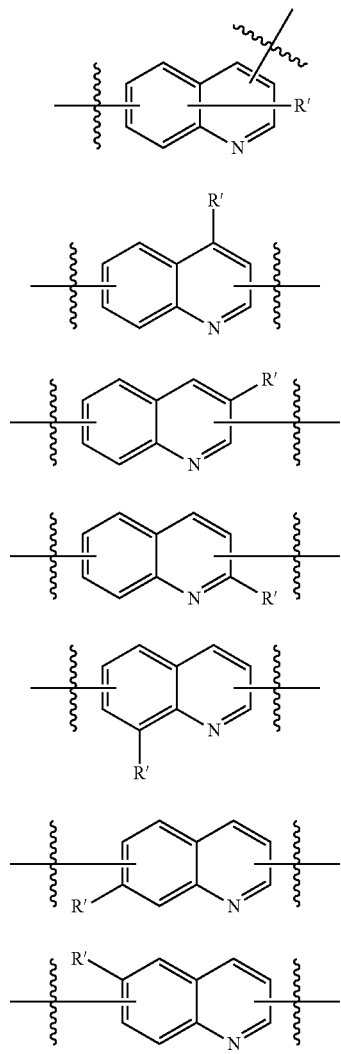

(Y)

(Y-1)

(Y-2)

(Y-3)

(Y-4)

(Y-5)

(Y-6)

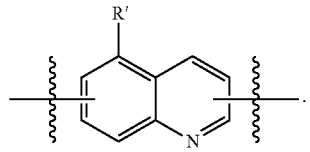

(Y-7)

In the present disclosure, halogen groups may be for example fluorine, chlorine, bromine or iodine.

In the present disclosure, aralkyl refers to a group having a

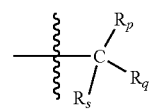

structure, wherein at least one of $R_p$, $R_q$ and $R_s$ is a substituted or unsubstituted aryl with 1 to 30 carbon atoms, and the rest is selected from a group consisting of the following groups: hydrogen, a linear alkyl with 1 to 20 carbon atoms, and a branched alkyl with 3 to 20 carbon atoms.

In one embodiment of the present disclosure, the nitrogen-containing organic compound has a structure represented by formula (1) as follows:

Formula (1)

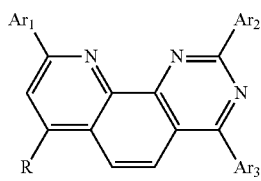

Wherein R is hydrogen or deuterium;

$Ar_1$, $Ar_2$ and $Ar_3$ are the same or different, and are each independently selected from a group consisting of the following groups: a substituted or unsubstituted aryl with 6 to 60 carbon atoms, a substituted or unsubstituted heteroaryl with 2 to 60 carbon atoms, and a substituted or unsubstituted aralkyl with 6 to 30 carbon atoms;

The substituents of $Ar_1$, $Ar_2$ and $Ar_3$ are the same or different, and are each independently selected from a group consisting of the following groups: deuterium, a halogen, a cyano, an alkyl with 1 to 10 carbon atoms, a cycloalkyl with 3 to 10 carbon atoms, a heterocycloalkyl with 2 to 10 carbon atoms, an aryl with 6 to 30 carbon atoms, a heteroaryl with 3 to 30 carbon atoms, an alkoxyl with 1 to 30 carbon atoms and an alkylsilyl with 1 to 30 carbon atoms.

In one embodiment of the present disclosure, the substituents of the $Ar_1$, $Ar_2$ and $Ar_3$ are the same or different, and are respectively independently selected from a group consisting of the following groups: deuterium; a fluorine; a cyano; an alkyl with 1 to 5 carbon atoms; an aryl with 6 to 16 carbon atoms optionally substituted by a phenyl, a naphthyl or a biphenyl; and a heteroaryl with 5 to 30 carbon atoms optionally substituted by a phenyl, a naphthyl or a biphenyl.

In one embodiment of the present disclosure, the substituents of the $Ar_1$, $Ar_2$ and $Ar_3$ are the same or different, and are respectively independently selected from a group consisting of the following groups: deuterium, a fluorine, a cyano, an alkyl with 1 to 5 carbon atoms, an aryl with 6 to 30 carbon atoms, and a heteroaryl with 3 to 30 carbon atoms.

In one embodiment of the present disclosure, $Ar_1$, $Ar_2$ and $Ar_3$ are the same or different, and are each independently selected from a group consisting of the following groups: a substituted or unsubstituted aryl with 6 to 35 carbon atoms, a substituted or unsubstituted heteroaryl with 3 to 35 carbon atoms, and a substituted or unsubstituted arylalkyl with 6 to 20 carbon atoms.

In one embodiment of the present disclosure, $Ar_1$, $Ar_2$ and $Ar_3$ are each independently selected from a group consisting of the following groups: a substituted or unsubstituted phenyl, a substituted or unsubstituted naphthyl, a substituted or unsubstituted biphenyl, a substituted or unsubstituted phenanthrenyl, a substituted or unsubstituted naphthylphenyl, a substituted or unsubstituted phenylnaphthyl, a substituted or unsubstituted phenanthrenylphenyl, a substituted or unsubstituted phenylphenanthrenyl, a substituted or unsubstituted triphenyl, a substituted or unsubstituted pyrenyl, a substituted or unsubstituted pyrenylphenyl, a substituted or unsubstituted phenylpyrenyl, a substituted or unsubstituted fluorenyl, a substituted or unsubstituted spirodifluorenyl, a substituted or unsubstituted anthracyl, a substituted or unsubstituted anthracylphenyl, a substituted or unsubstituted phenylanthracyl, a substituted or unsubstituted triphenylidene, a substituted or unsubstituted 1,3,5-triphenylphenyl, a substituted or unsubstituted quinolyl, a substituted or unsubstituted isoquinolyl, a substituted or unsubstituted pyridinyl, a substituted or unsubstituted carbazolyl, a substituted or unsubstituted carbazolylphenyl, a substituted or unsubstituted phenylcarbazolyl, a substituted or unsubstituted triazinyl, a substituted or unsubstituted dibenzofuranyl, a substituted or unsubstituted dibenzothiophenyl, a substituted or unsubstituted dibenzofuranyl phenyl, a substituted or unsubstituted dibenzofuranylphenyl, and a substituted or unsubstituted dibenzothiophenylphenyl.

In one embodiment of the present disclosure, the $Ar_1$, $Ar_2$ and $Ar_3$ are the same or different, and are each independently selected from a group consisting of the following groups:

wherein

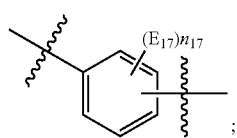

represents a chemical bond;
$M_1$ is selected from a single bond or

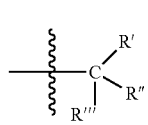 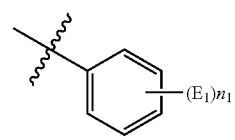

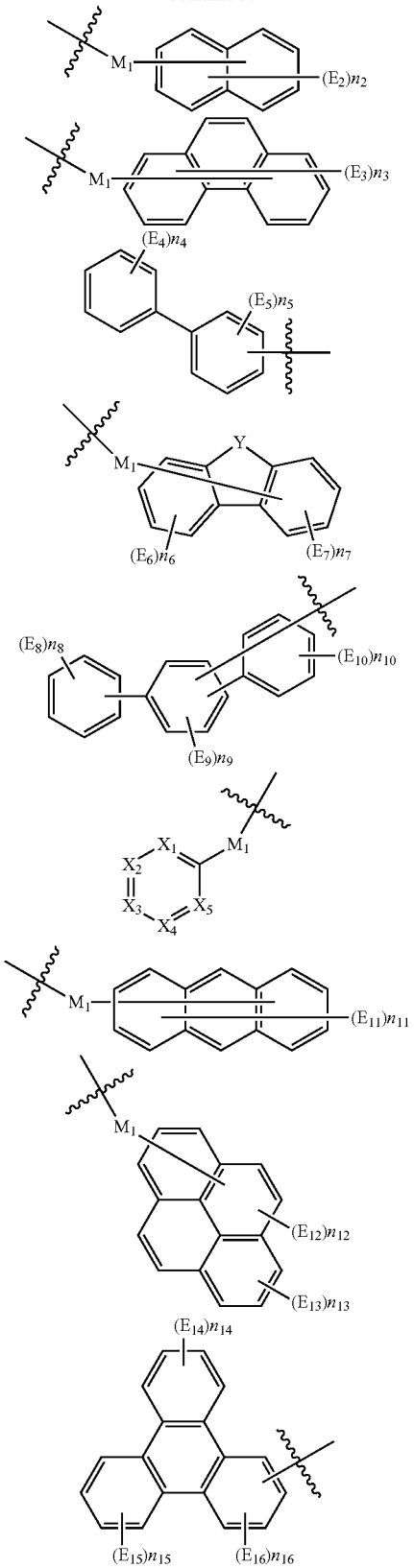

R', R" and R"' are the same or different, and are each independently selected from a group consisting of the following groups: hydrogen, an alkyl with 1 to 3 carbon atoms and an aryl with 6 to 12 carbon atoms, and at least one of R', R" and R'" is aryl;

$n_1$, $n_4$, $n_8$ and $n_{10}$ are the same or different, and are respectively independently 0, 1, 2, 3, 4 or 5;

$n_2$ is 0, 1, 2, 3, 4, 5, 6 or 7;

$n_3$ and $n_{11}$ are the same or different, and are respectively independently 0, 1, 2, 3, 4, 5, 6, 7, 8 or 9;

$n_5$, $n_6$, $n_7$, $n_9$, $n_{14}$, $n_{15}$ and $n_{17}$ are the same or different, and are respectively independently 0, 1, 2, 3 or 4;

$n_{12}$ is 0, 1 or 2;

$n_{13}$ and $n_{16}$ are the same or different, and are respectively independently 0, 1, 2 or 3;

Y is O, S, $C(E_{18}E_{19})$, $Si(E_{20}E_{21})$, $N(E_{22})$ or Se;

$E_1$ to $E_{22}$ are the same or different, and are respectively independently selected from a group consisting of the following groups: hydrogen, deuterium, a halogen, a cyano, an alkyl with 1 to 10 carbon atoms, an aryl with 6 to 30 carbon atoms, a heteroaryl with 3 to 30 carbon atoms and a cycloalkyl with 3 to 10 carbon atoms; alternatively, $E_{18}$ and $E_{19}$ are connected to form a ring, or $E_{20}$ and $E_{21}$ are connected to form a ring, wherein $E_1$, $E_4$, $E_5$ and $E_{17}$ cannot be aryl;

$X_1$ to $X_5$ are the same or different, and are respectively independently selected from C(R') or N, and at least one of $X_1$ to $X_5$ is N, wherein R's in $X_1$ to $X_5$ are the same or different, and are respectively independently selected from a group consisting of the following groups: hydrogen, an alkyl with 1 to 10 carbon atoms, an aryl with 6 to 18 carbon atoms, a heteroaryl with 3 to 18 carbon atoms and a cycloalkyl with 3 to 10 carbon atoms, or adjacent R's are connected to form a ring.

In the present disclosure, $n_1$ is the number of substituents $E_1$, and when $n_1$ is greater than or equal to 2, any two $E_1$s are the same or different; $n_2$ is the number of substituents $E_2$, and when $n_2$ is greater than or equal to 2, any two $E_2$s are the same or different; $n_3$ is the number of substituents $E_3$, and when $n_3$ is greater than or equal to 2, any two $E_3$s are the same or different; $n_4$ is the number of substituents $E_4$, and when $n_4$ is greater than or equal to 2, any two $E_4$s are the same or different; $n_5$ is the number of substituents $E_5$, and when $n_5$ is greater than or equal to 2, any two $E_5$s are the same or different; $n_6$ is the number of substituents $E_6$, and when $n_6$ is greater than or equal to 2, any two $E_6$s are the same or different; $n_7$ is the number of substituents $E_7$, and when $n_7$ is greater than or equal to 2, any two $E_7$s are the same or different; $n_8$ is the number of substituents $E_8$, and when $n_8$ is greater than or equal to 2, any two $E_8$s are the same or different; $n_9$ is the number of substituents $E_9$, and when $n_9$ is greater than or equal to 2, any two $E_9$s are the same or different; $n_{10}$ is the number of substituents $E_{10}$, and when $n_{10}$ is greater than or equal to 2, any two $E_{10}$s are the same or different; $n_{11}$ is the number of substituents $E_{11}$, and when $n_{11}$ is greater than or equal to 2, any two $E_{11}$s are the same or different; $n_{12}$ is the number of substituents $E_{12}$, and when $n_{12}$ is greater than or equal to 2, any two $E_{12}$s are the same or different; $n_{13}$ is the number of substituents $E_{13}$, and when $n_{13}$ is greater than or equal to 2, any two $E_{13}$s are the same or different; $n_{14}$ is the number of substituents $E_{14}$, and when $n_{14}$ is greater than or equal to 2, any two $E_{14}$s are the same or different; $n_{15}$ is the number of substituents $E_{15}$, and when $n_{15}$ is greater than or equal to 2, any two $E_{15}$s are the same or different; $n_{16}$ is the number of substituents $E_{16}$, and when $n_{16}$ is greater than or equal to 2, any two $E_{16}$s are the same or different; $n_{17}$ is the number of substituents $E_{17}$, and when $n_{17}$ is greater than or equal to 2, any two $E_{17}$s are the same or different.

In the present disclosure, an aromatic ring is not substituted when $n_1$ to $n_{17}$ are 0 respectively.

In the present disclosure, the meaning of A and B "can be connected to form a ring" includes that A and B are independent of each other and not connected; and it also includes that A and B are connected with each other to form a ring. For example, $E_{18}$ and $E_{19}$ can be connected to form a ring, including the way in which $E_{18}$ and $E_{19}$ are mutually independent and not connected, and the way in which $E_{18}$ and $E_{19}$ are mutually connected to form a ring; $E_{20}$ and $E_{21}$ can be connected to form a ring, including the way in which $E_{20}$ and $E_{21}$ are mutually independent and not connected, and the way in which $E_{20}$ and $E_{21}$ are mutually connected to form a ring.

Adjacent R's can be connected to form a ring, which means that $X_1$ and $X_2$ form a ring, or $X_2$ and $X_3$ form a ring, or $X_3$ and $X_4$ form a ring, or $X_4$ and $X_5$ form a ring, of course, it also includes cases such as $X_3$ and $X_4$ form a ring and $X_1$ and $X_2$ form a ring.

For example, $X_3$ and $X_4$ can be connected to form a ring, including the way in which R' of $X_3$ and R' of $X_4$ are mutually independent and not connected, and the way in which R' of $X_3$, R' of $X_4$ and atoms connected by R' are connected to form a ring.

In the present disclosure, the ring refers to, but is not limited to, a saturated or unsaturated ring, such as

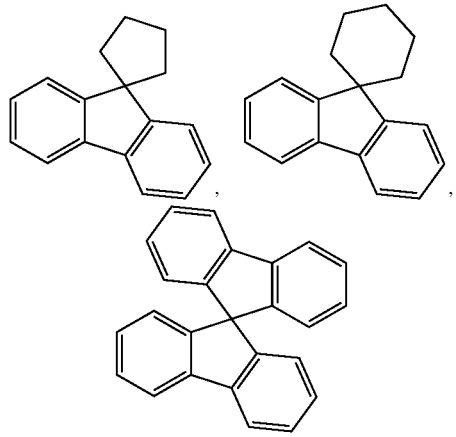

and the like.

Optionally, the ring formed above is a 3- to 10-membered ring.

In one embodiment of the present disclosure, the $Ar_1$, $Ar_2$ and $Ar_3$ are the same or different, and are each independently selected from a group consisting of the following groups: a substituted or unsubstituted aryl with 6 to 20 carbon atoms, a substituted or unsubstituted heteroaryl with 3 to 25 carbon atoms, and a substituted or unsubstituted arylalkyl with 6 to 20 carbon atoms.

In one embodiment of the present disclosure, the substituents of the $Ar_1$, $Ar_2$ and $Ar_3$ are the same or different, and are respectively independently selected from a group consisting of the following groups: deuterium; a fluorine; a cyano; a methyl; an ethyl; an isopropyl; a tert-butyl; a naphthyl; a dibenzofuranyl; a dibenzothiophenyl; a N-phenylcarbazolyl optionally substituted by a phenyl; an anthracyl; a N-naphthylcarbazolyl; a pyrenyl; a phenyl optionally substituted by a phenyl or a naphthyl; a biphenyl; a triazinyl optionally substituted by a phenyl, a naphthyl or a biphenyl; a pyridyl; and a phenanthrenyl.

In one embodiment of the present disclosure, the $Ar_1$, $Ar_2$ and $Ar_3$ are the same or different, and are each independently selected from a group consisting of the following groups:
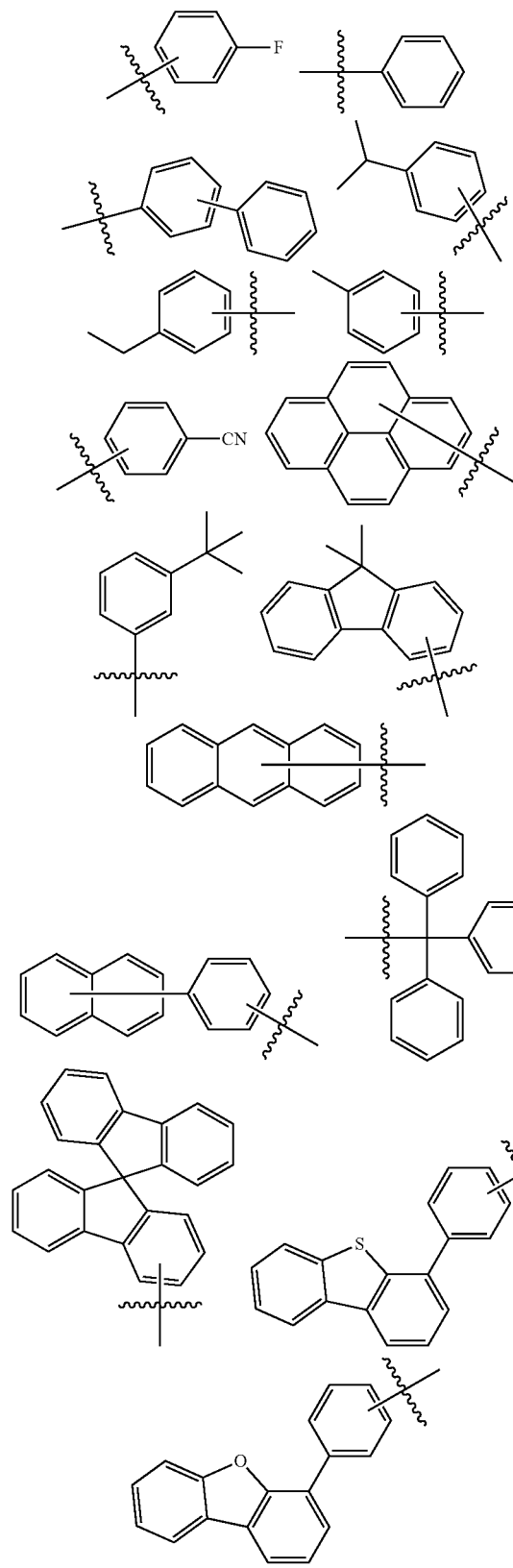
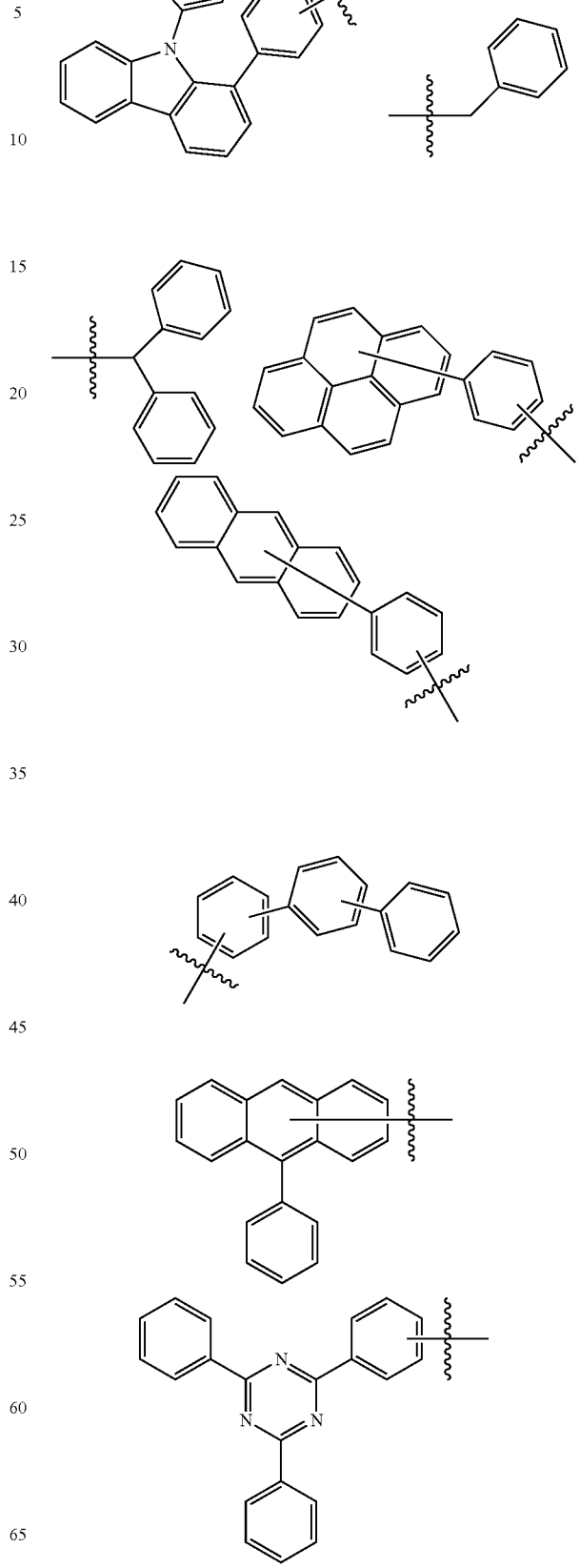

-continued
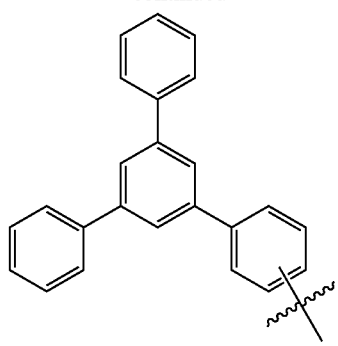
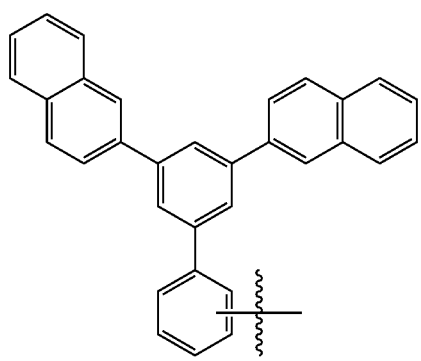
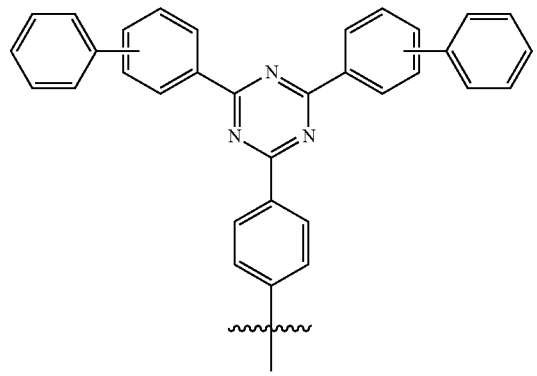
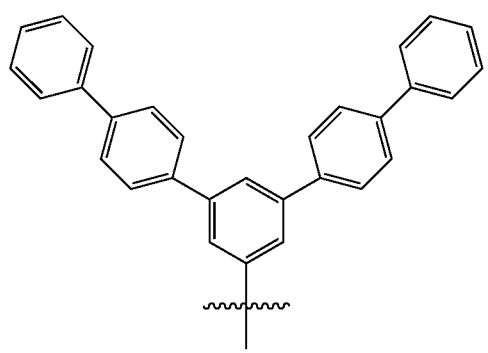
-continued
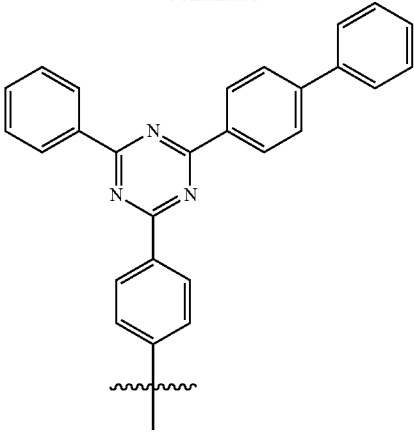
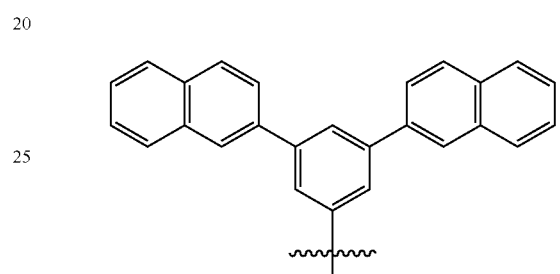
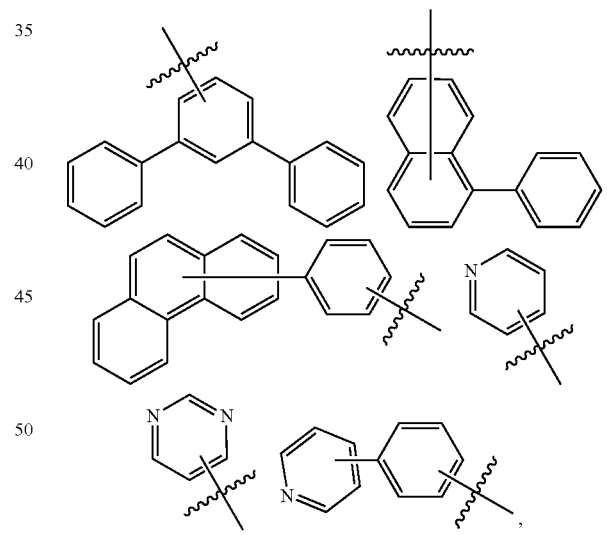
wherein
represents a chemical bond.
In one embodiment of the present disclosure, the $Ar_1$, $Ar_2$ and $Ar_3$ are the same or different, and are each independently selected from a group consisting of the following groups:

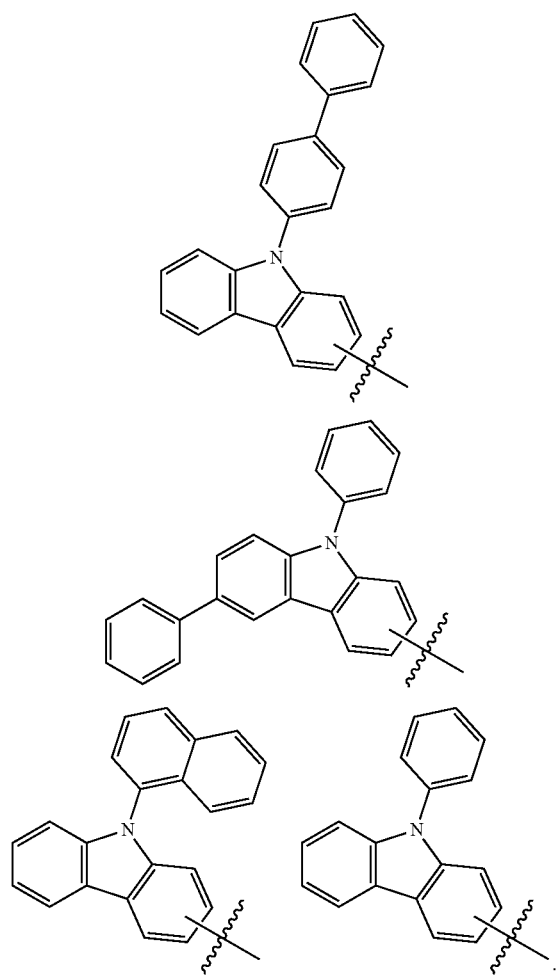
In one embodiment of the present disclosure, the $Ar_1$, $Ar_2$ and $Ar_3$ are the same or different, and are each independently selected from a group consisting of the following groups:
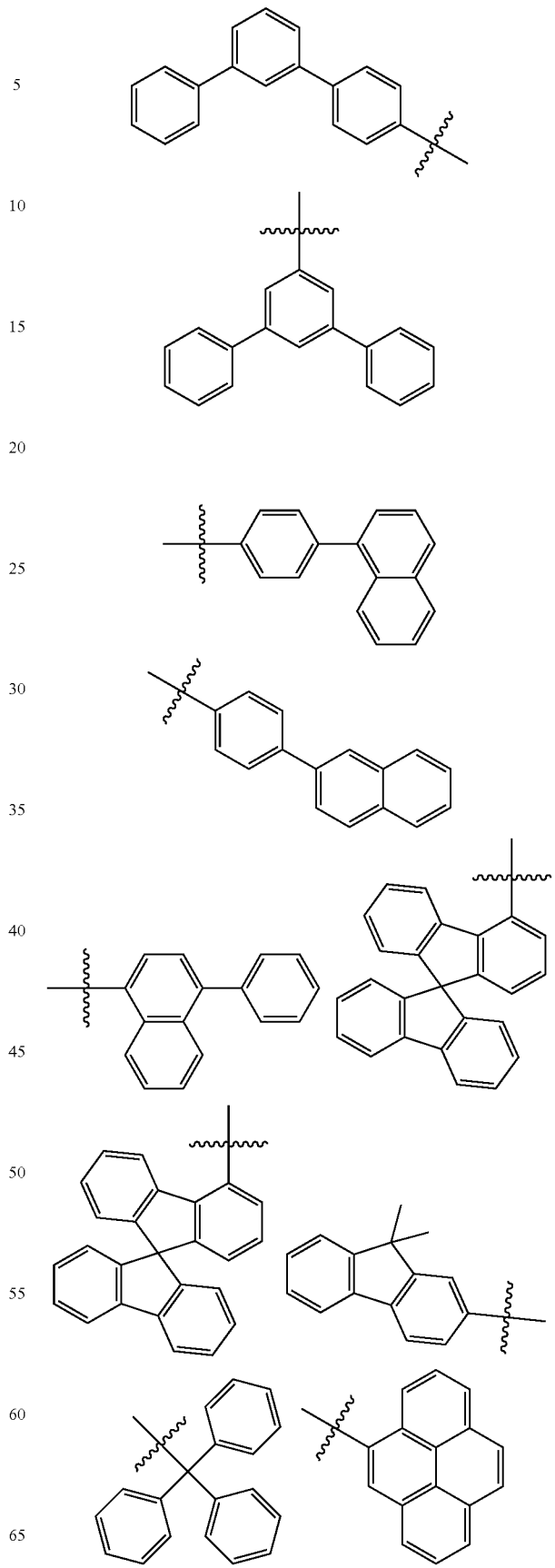

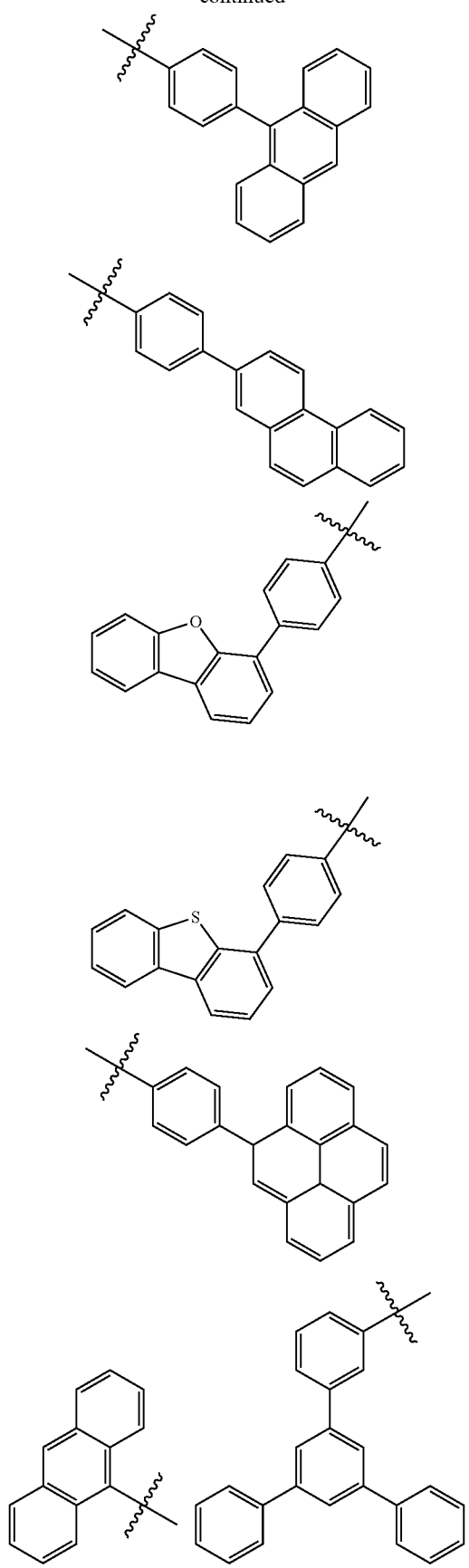
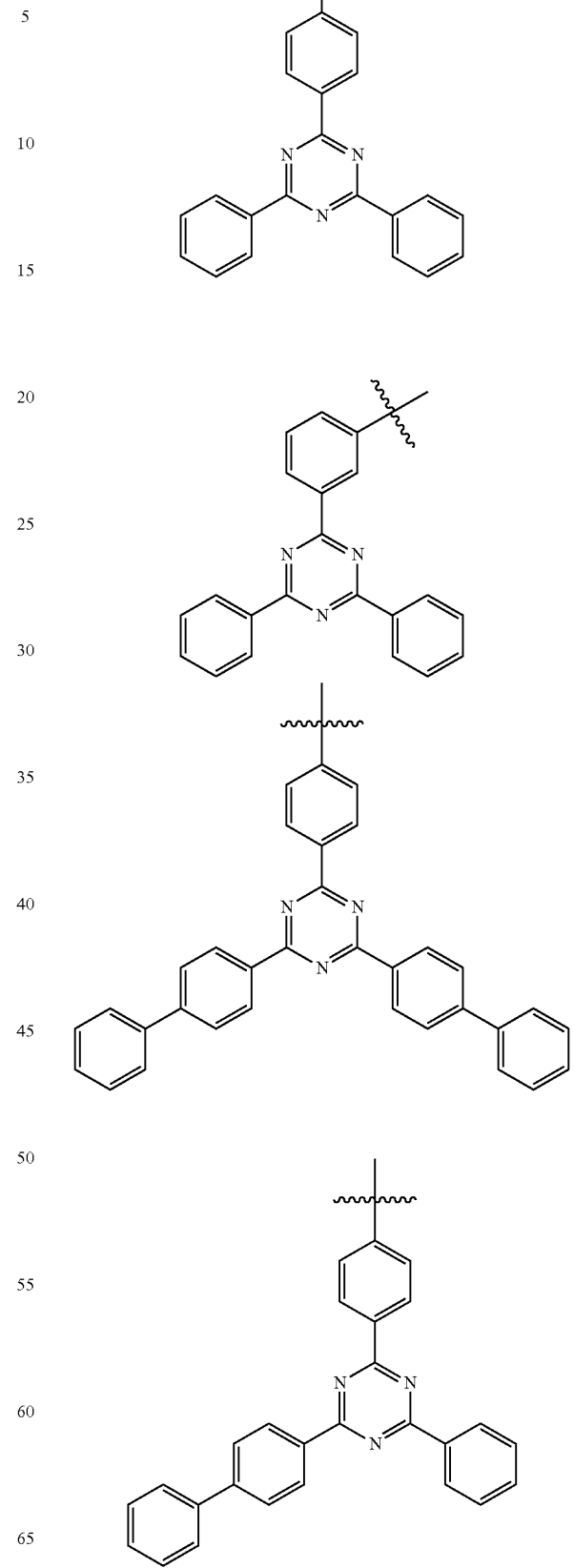

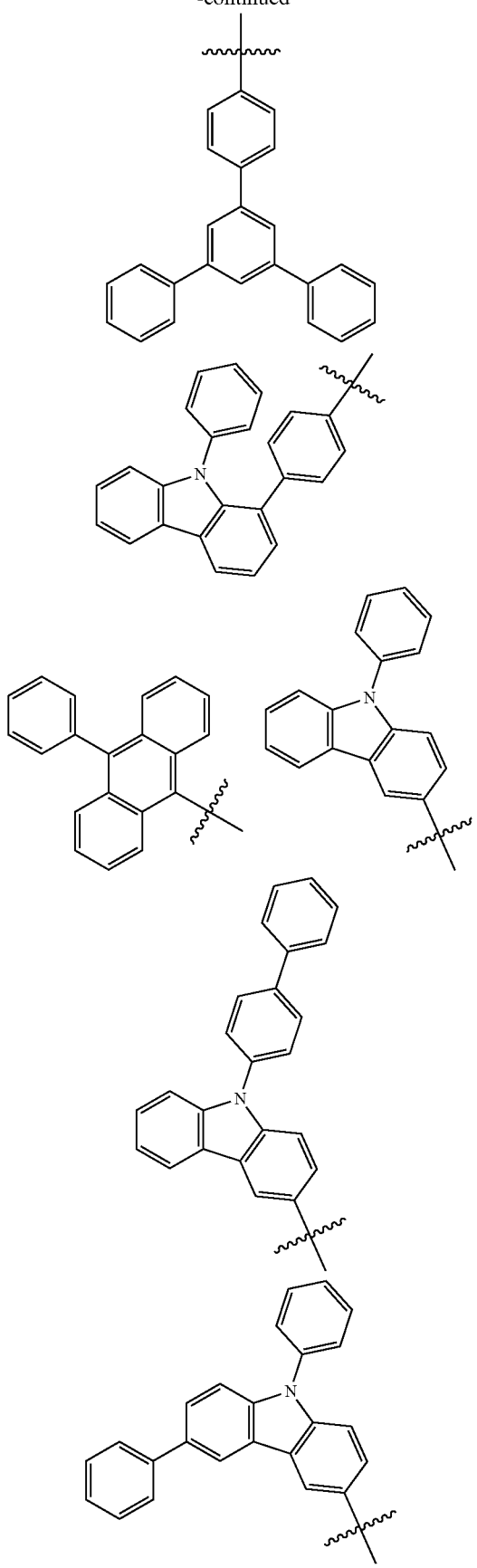
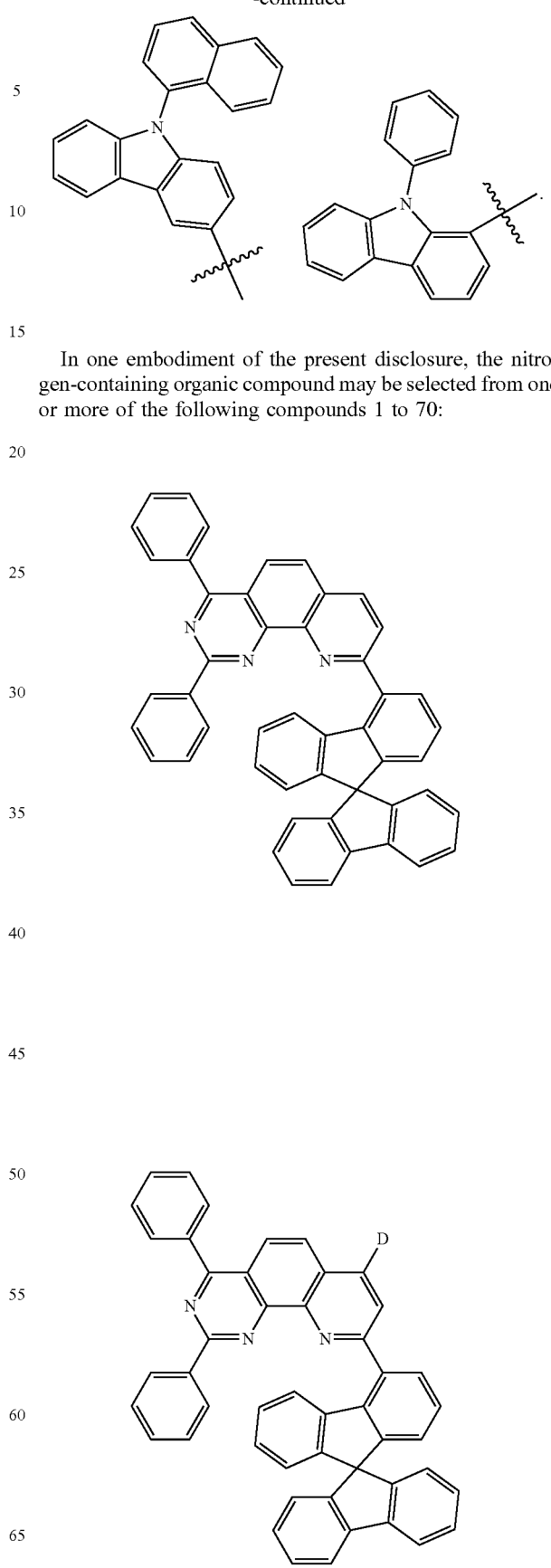
In one embodiment of the present disclosure, the nitrogen-containing organic compound may be selected from one or more of the following compounds 1 to 70:

-continued
3
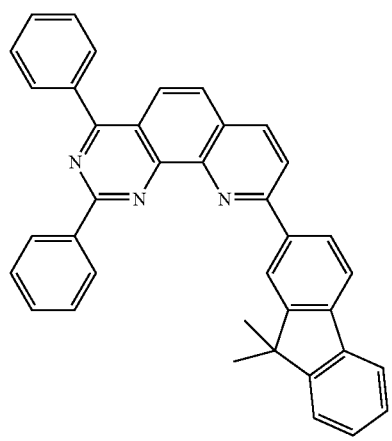
4
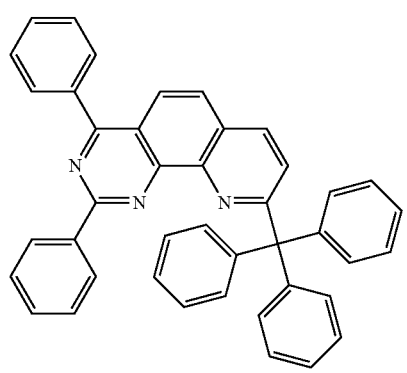
5
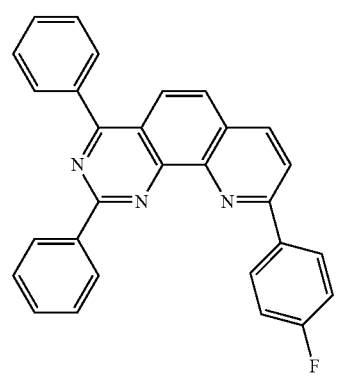
6
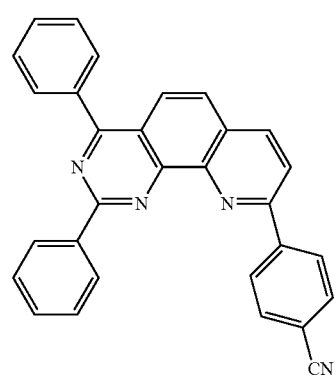
-continued
7
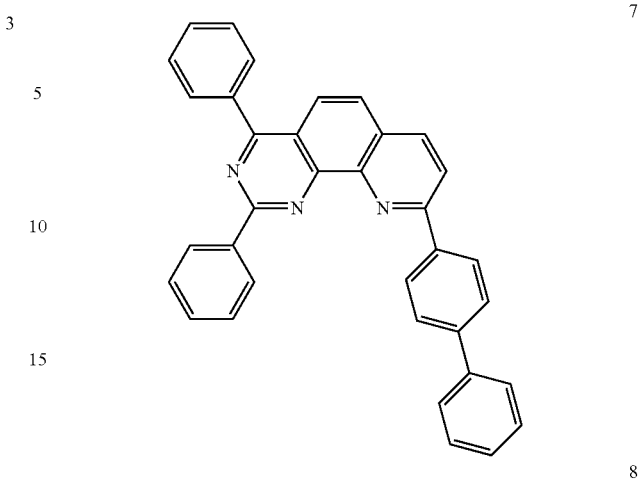
8
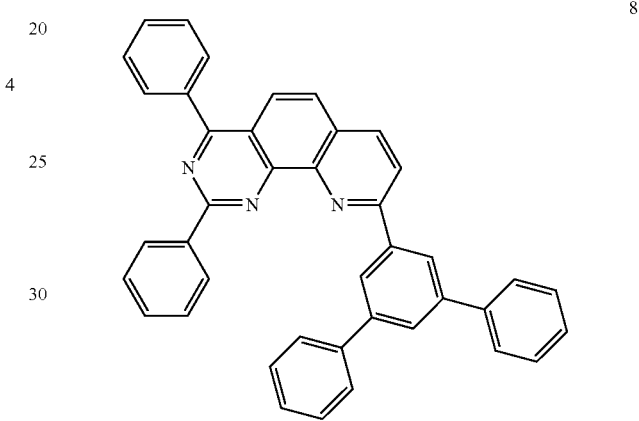
9
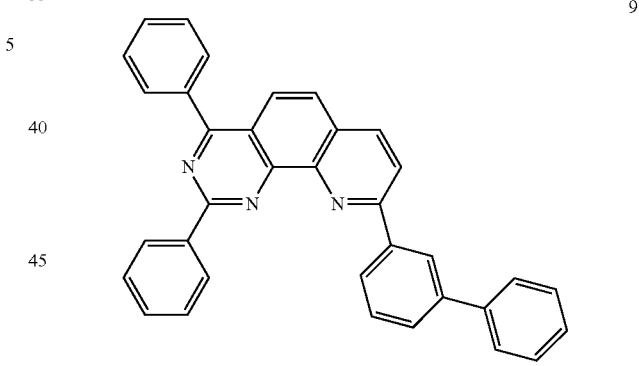
10
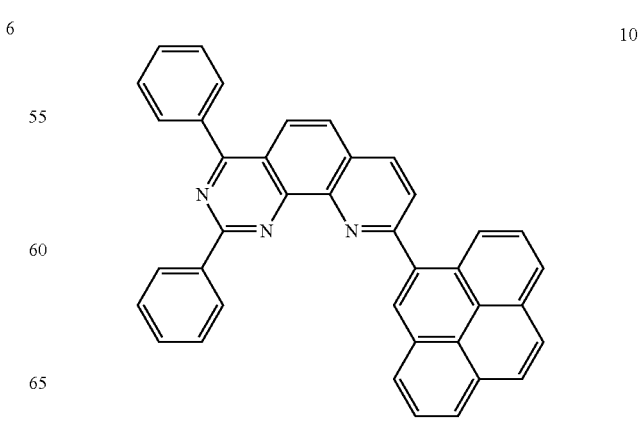

11
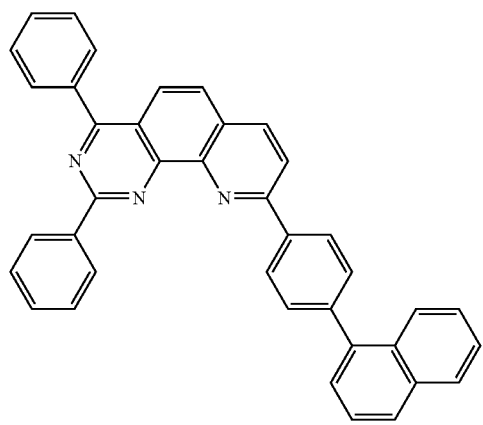
12
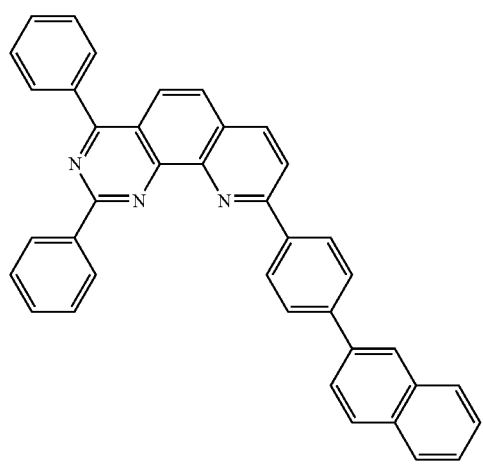
13
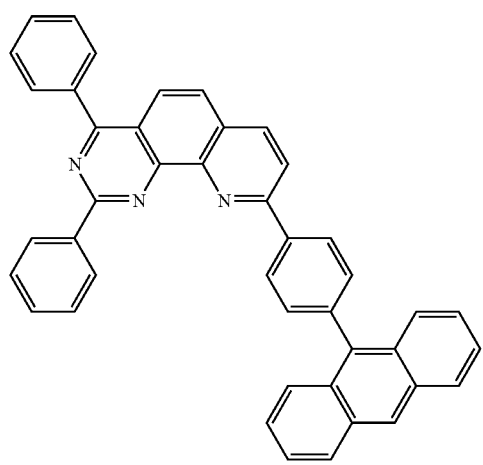
14
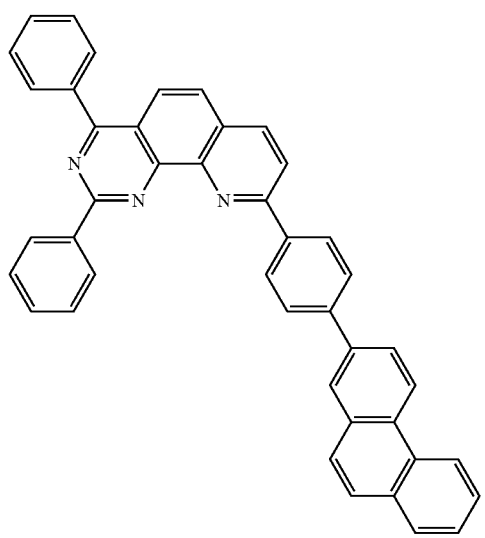
15
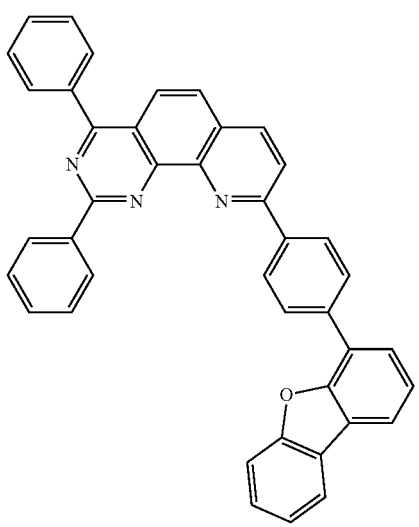
16
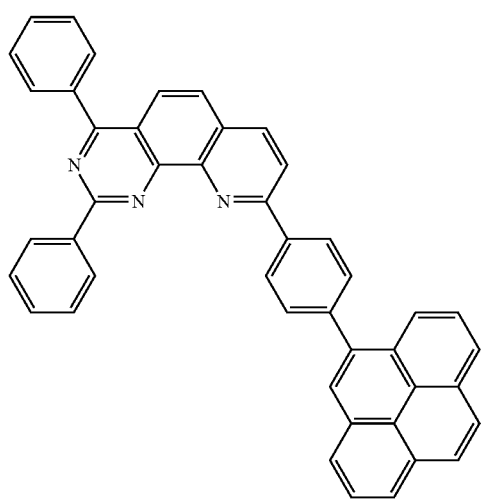

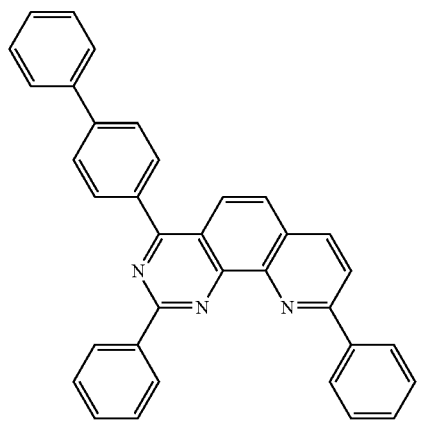
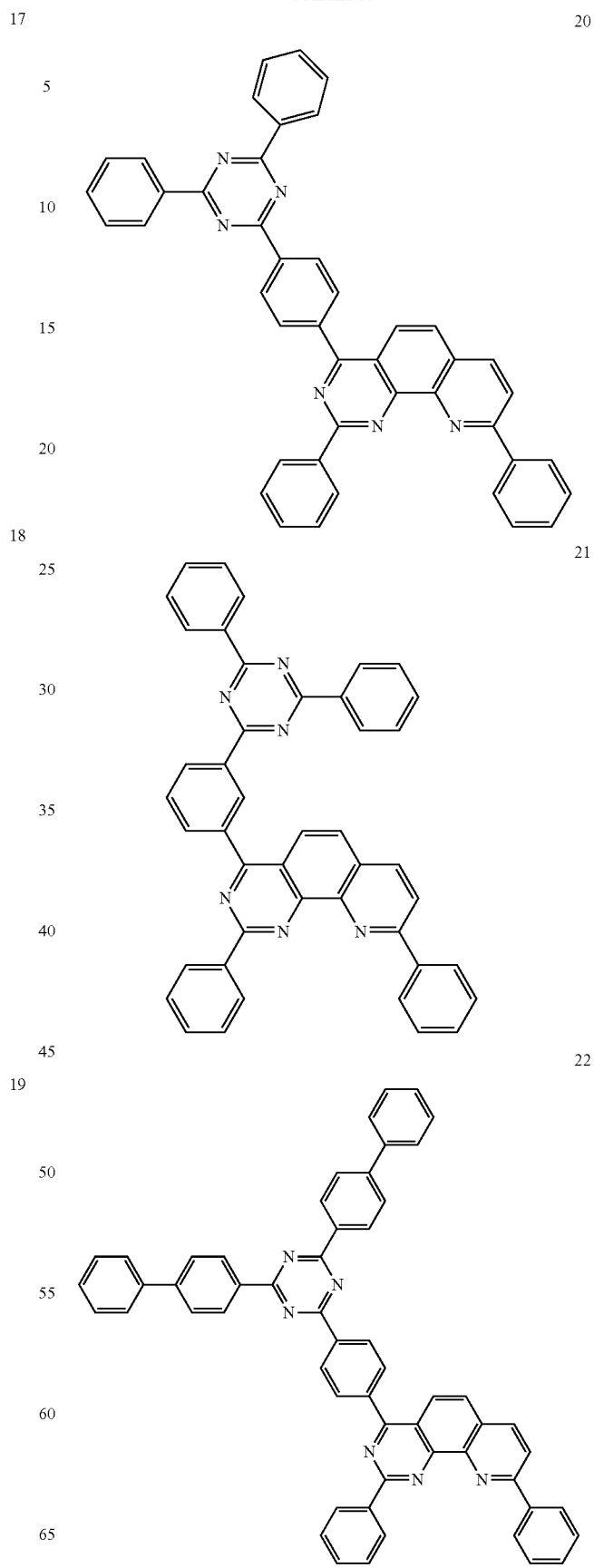

23
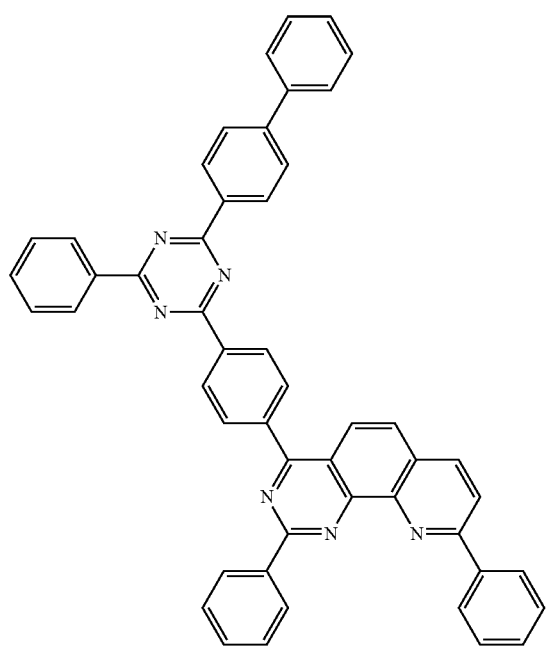
24
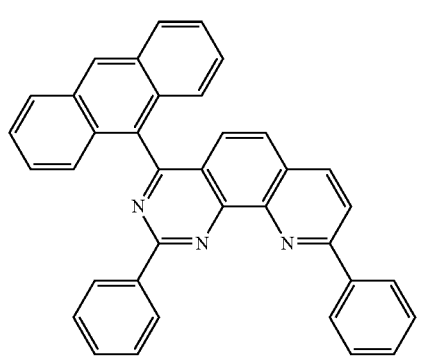
25
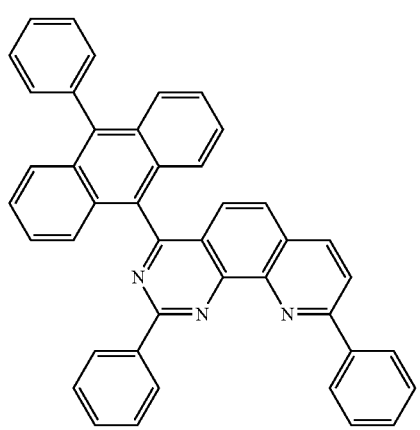
26
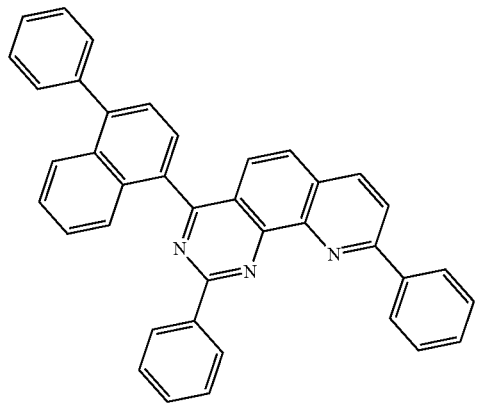
27
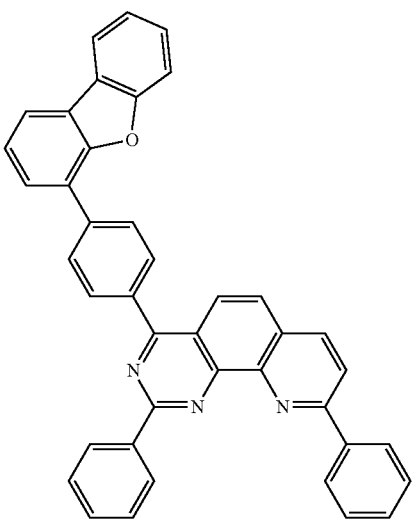
28
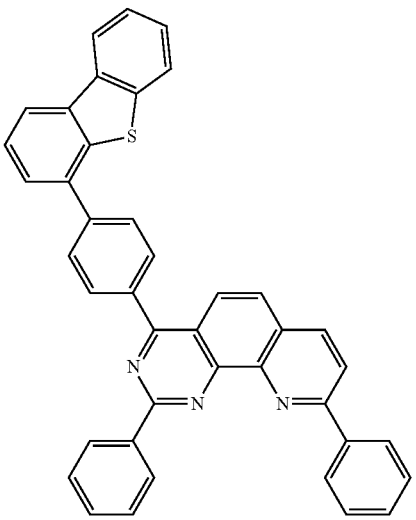

29
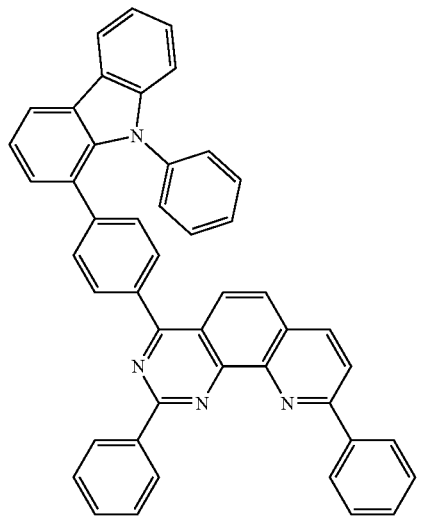
30
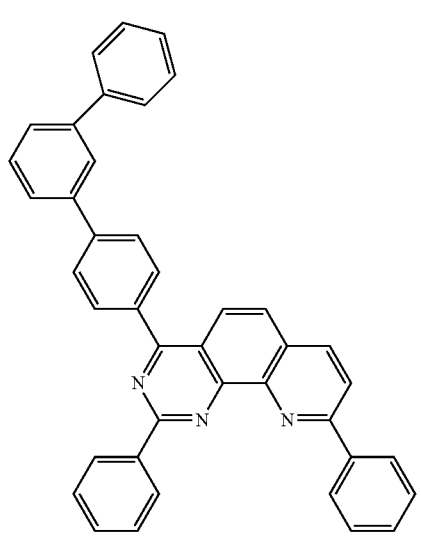
31
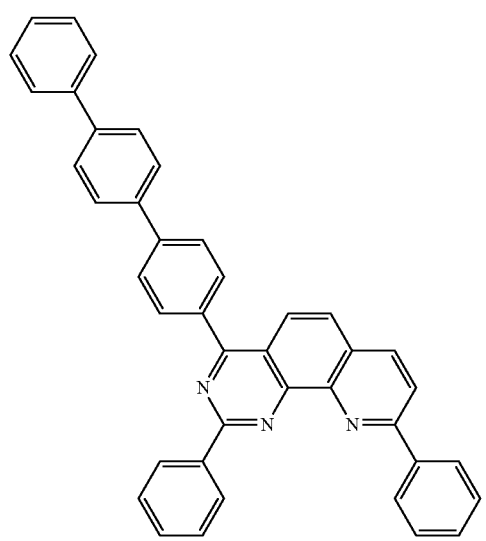
32
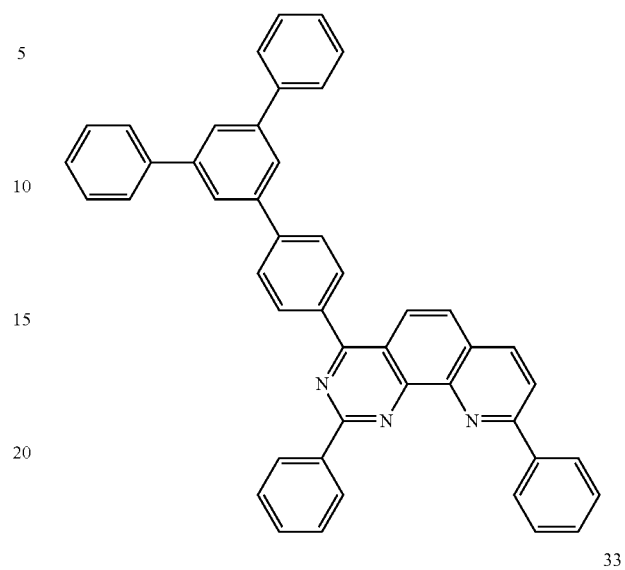
33
34
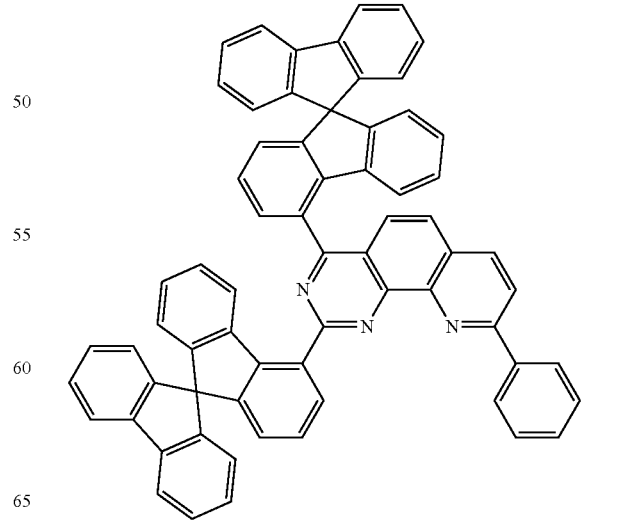

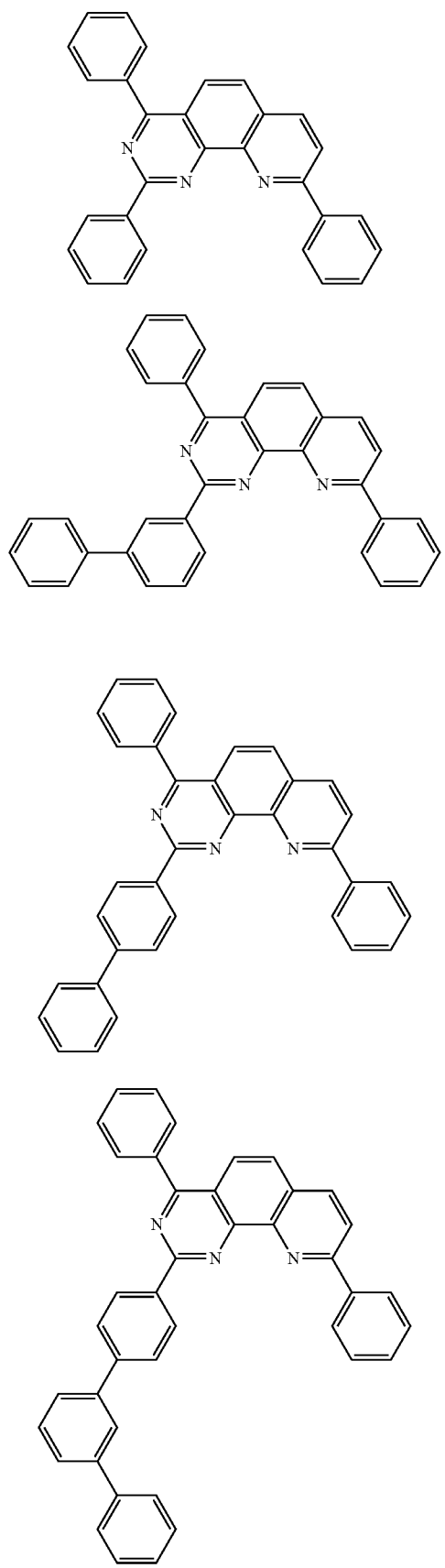
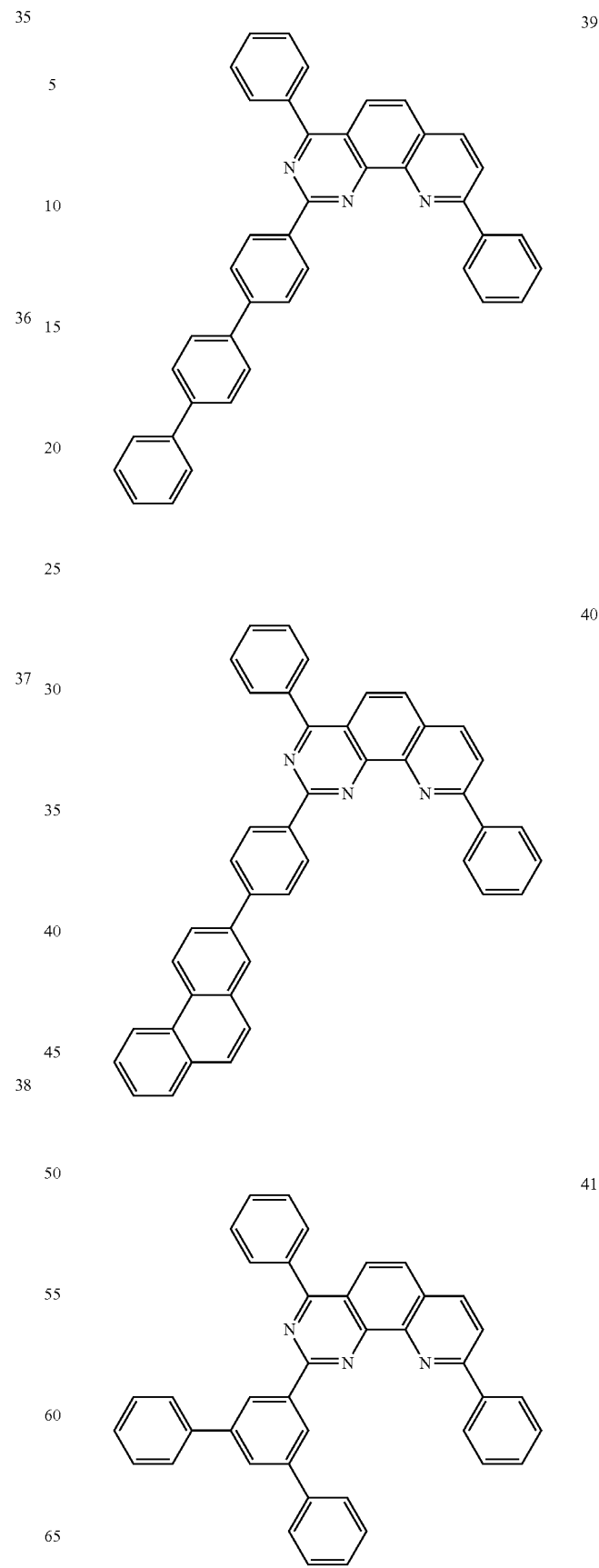

42
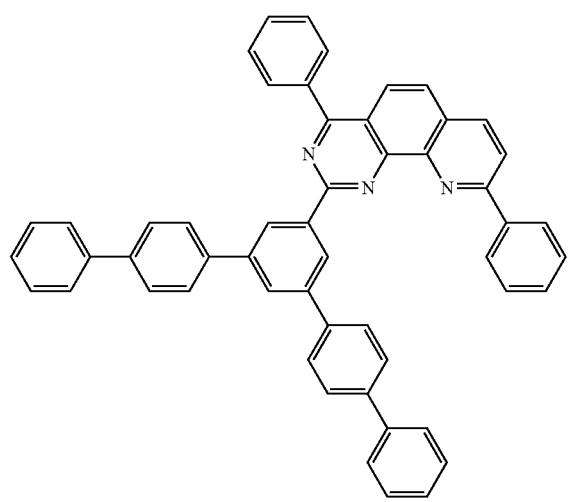
43
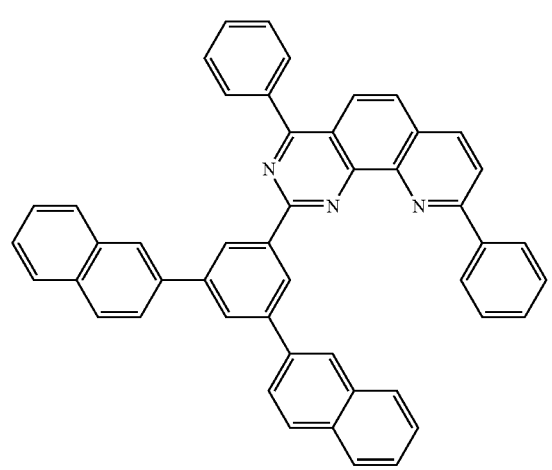
44
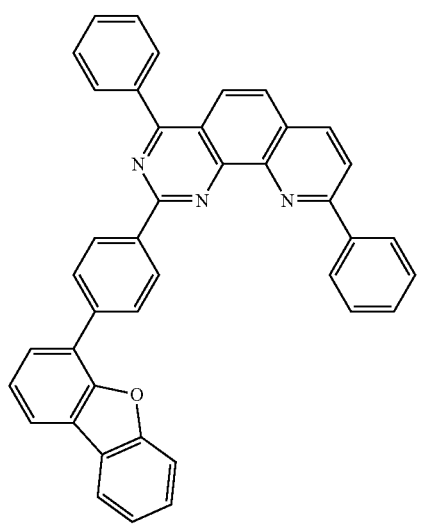
45
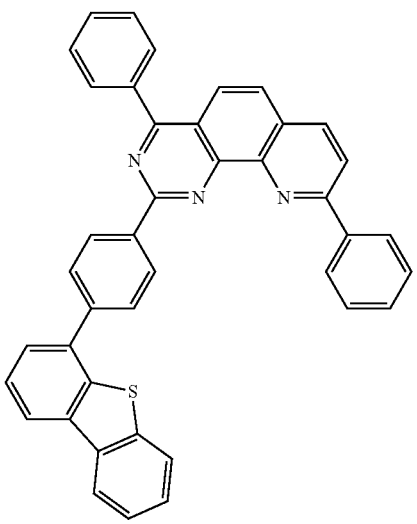
46
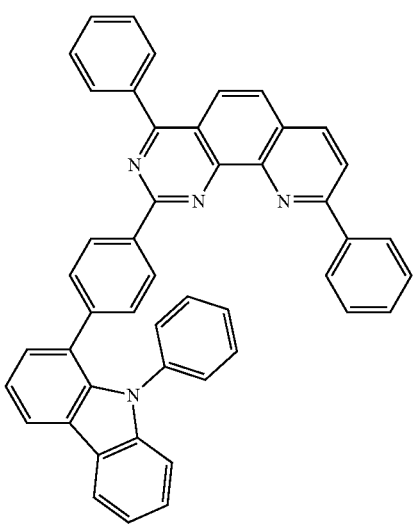
47
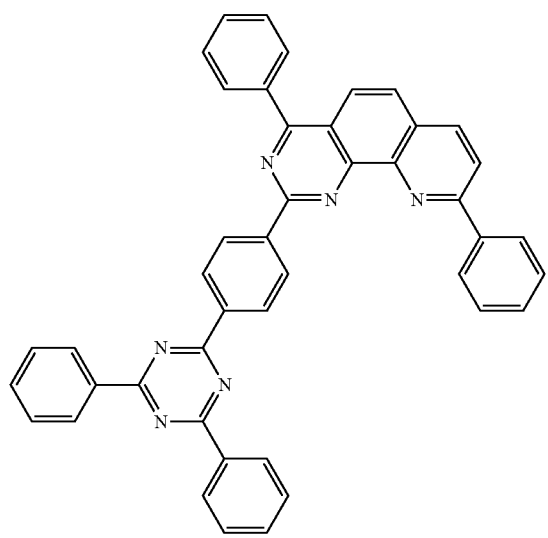

48
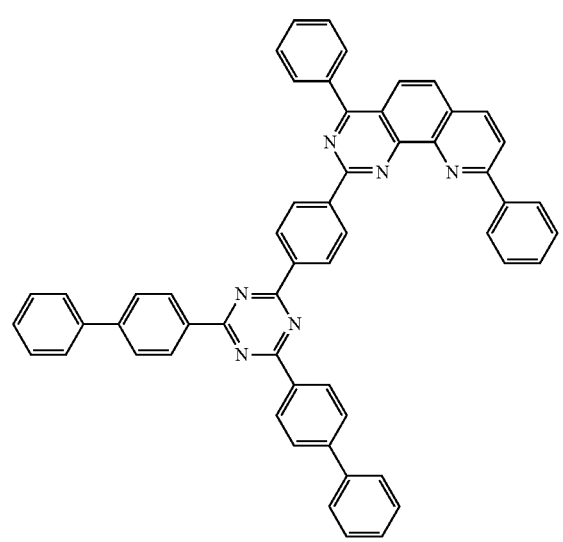
49
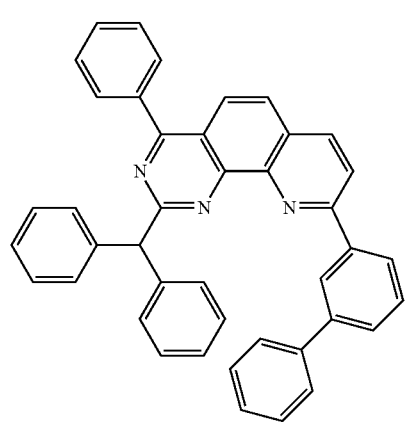
50
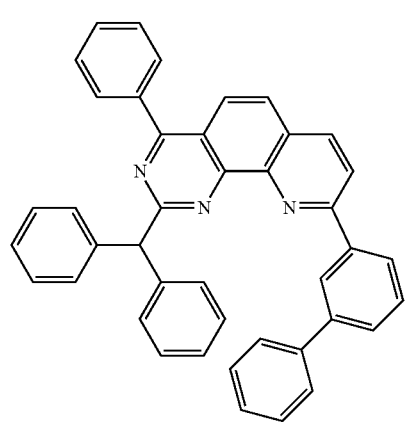
51
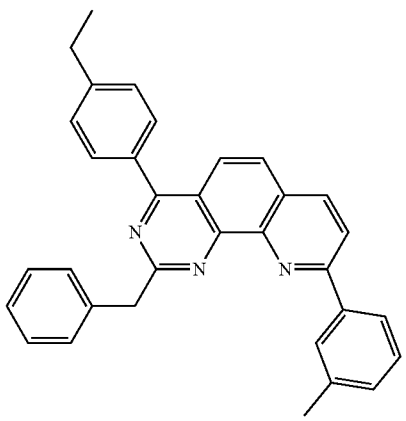
52
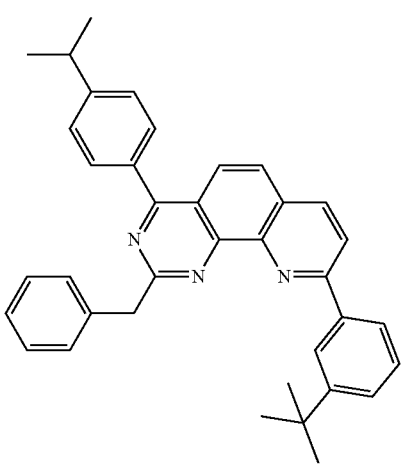
53
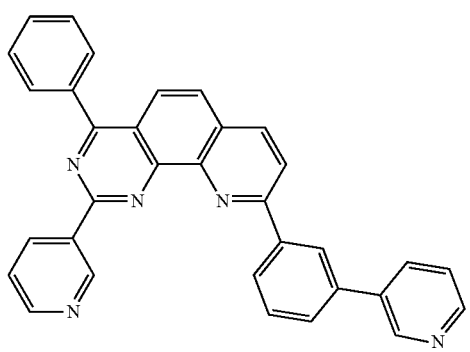
54
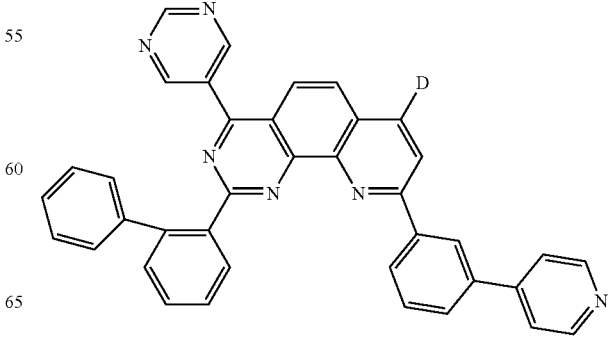

55
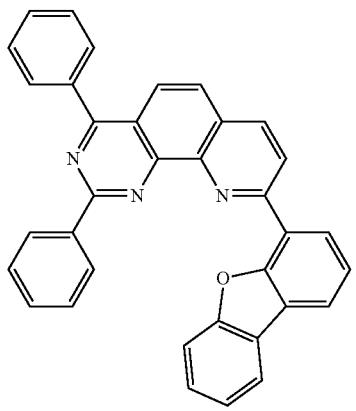
56
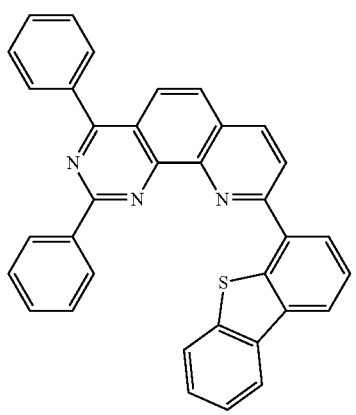
57
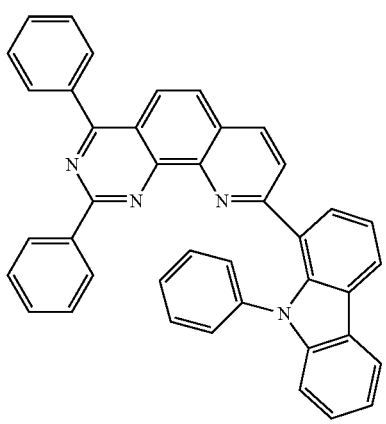
58
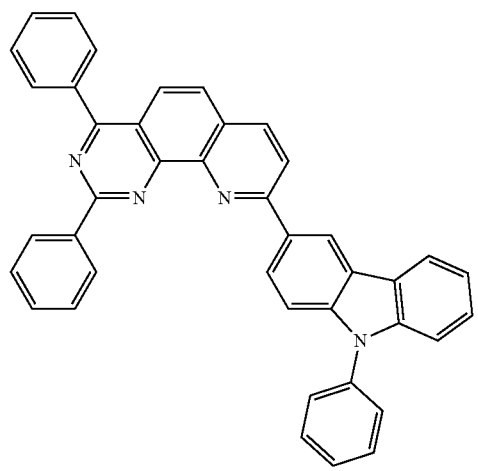
59
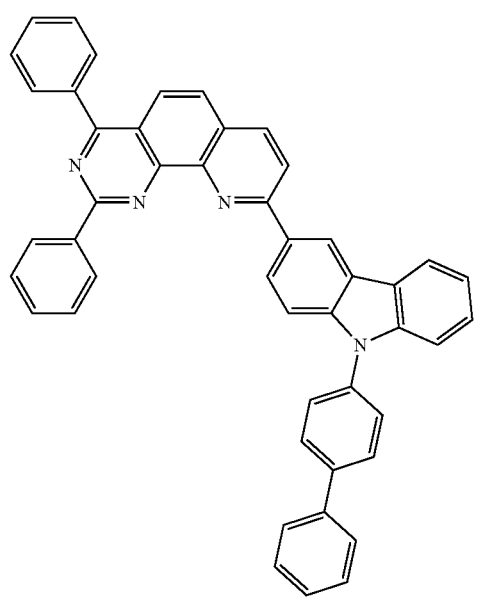
60
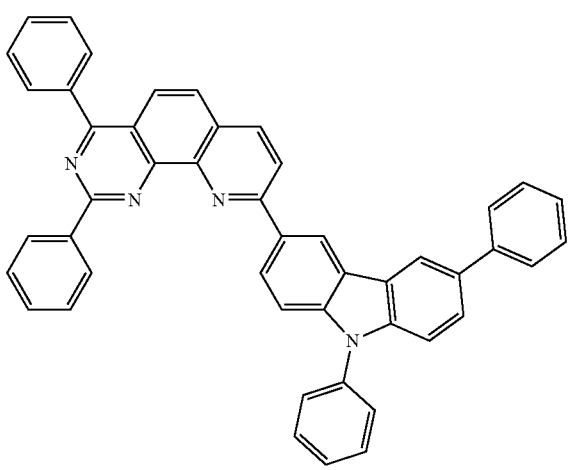

61
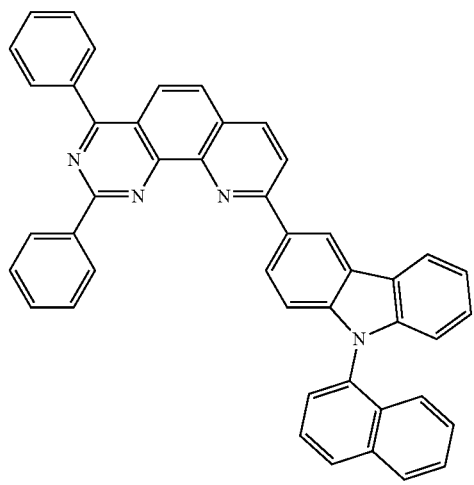
62
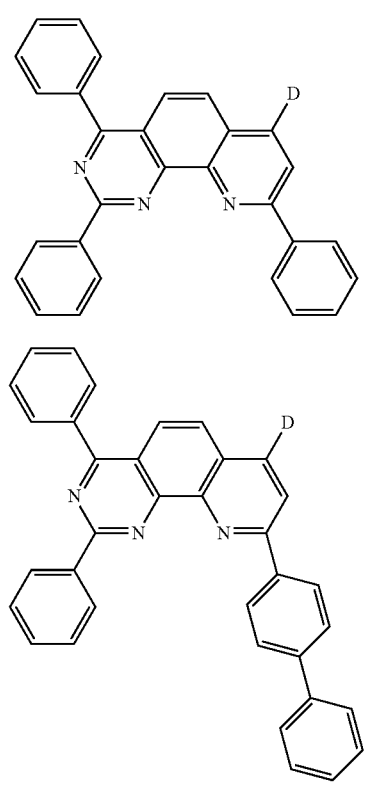
63
64
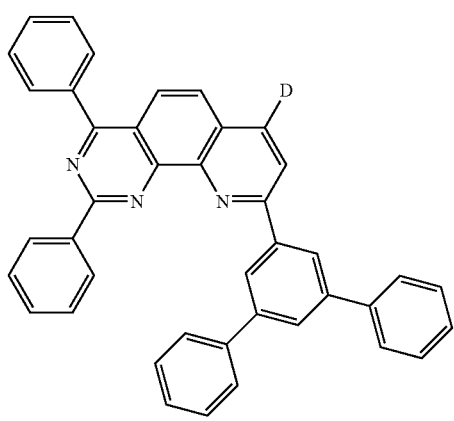
65
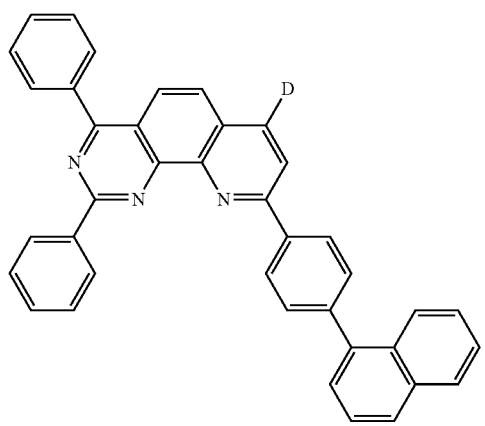
66
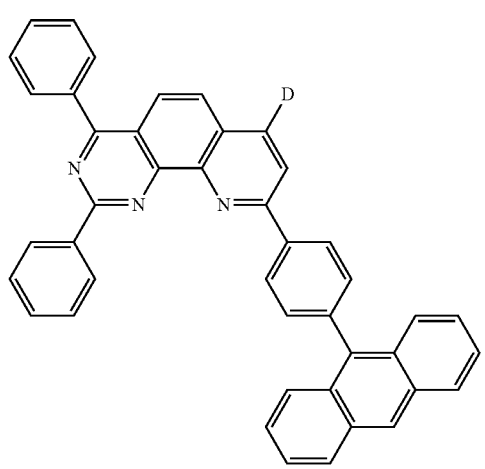
67
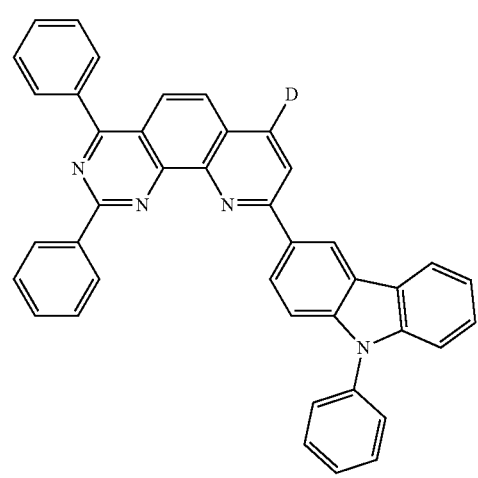

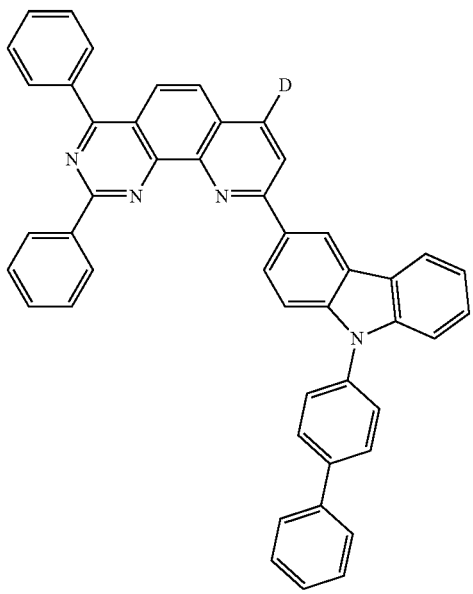

68

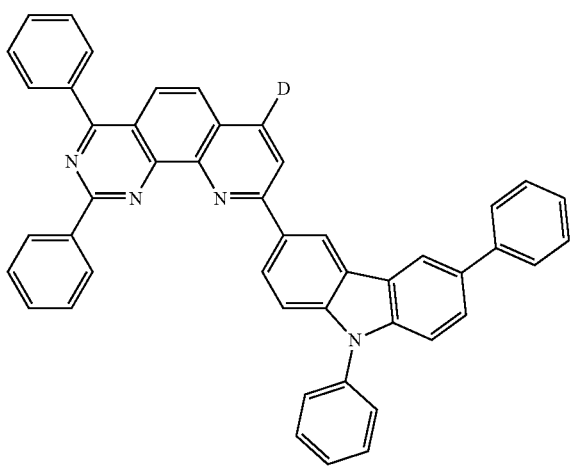

69

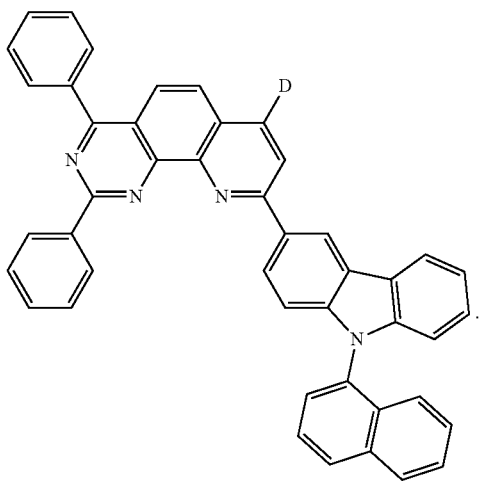

70

A second aspect of the present disclosure provides a use of the nitrogen-containing organic compound described in the first aspect of the present disclosure in an organic electroluminescent device.

According to the present disclosure, the nitrogen-containing organic compound has a good electron transport performance and thermal stability, and can be used as an electron transport material of the organic electroluminescent device.

A third aspect of the present disclosure provides an organic electroluminescent device comprising an anode, a cathode and at least one functional layer between the anode and the cathode, wherein the functional layer comprises a hole injection layer, a hole transport layer, an organic electroluminescent layer, an electron transport layer and an electron injection layer, and the electron transport layer may contain the nitrogen-containing organic compound described in the first aspect of the present disclosure.

In one embodiment, as shown in FIG. 1, the organic electroluminescent device of the present disclosure comprises an anode 100, a cathode 200 and at least one functional layer 300 between the anode layer and the cathode layer, wherein the functional layer 300 comprises a hole injection layer 310, a hole transport layer 320, an organic electroluminescent layer 330, an electron transport layer 350 and an electron injection layer 360, the hole injection layer 310, the hole transport layer 320, the organic electroluminescent layer 330, the electron transport layer 350 and the electron injection layer 360 can be formed on the anode 100 successively, and the electron transport layer 350 may contain the nitrogen-containing organic compound described in the first aspect of the present disclosure, preferably at least one of compounds 1~54.

In a further embodiment, the nitrogen-containing compound of the present disclosure may be used as the host material of the light-emitting layer.

In a further embodiment, the functional layer 300 of the organic electroluminescent device may also comprise a hole-blocking layer 340 and an electron-blocking layer 370, wherein the hole-blocking layer 340 may be arranged between the organic electroluminescent layer 330 and the electron transport layer 350, and the electron-blocking layer 370 may be arranged between the hole transport layer 320 and the organic electroluminescent layer 330.

The organic electroluminescent device of the present disclosure is based on the excellent performance of the nitrogen-containing organic compound of the present disclosure, and devices obtained from the compound as the electron transport layer material can reduce the driving voltage of the organic electroluminescent device, improve the luminous efficiency and prolong the lifetime of the device.

The present disclosure will be described in further details below by embodiments. However, the following embodiments are only illustrations of the present disclosure and are not intended to limit the present disclosure.

Synthesis Example

Those skilled in the art will be aware of that: the chemical reactions described herein can be used to appropriately prepare many other compounds of the present disclosure, and other methods for preparing the compound of the present disclosure are considered to fall within the scope of the present disclosure. For example, the synthesis of those non-illustrative compounds according to the present disclosure can be successfully completed by those skilled in the art through modification methods, such as appropriate protection of interfering groups, use of other known reagents except for those described in the present disclosure, or making some conventional modifications to the reaction conditions. Additionally, the reactions or known reaction conditions disclosed in the present disclosure are also accepted as applicable to the preparation of other compounds of the present disclosure.

Unless otherwise indicated, all temperatures in the embodiments described below are set in Celsius degrees. Reagents were purchased from commodity suppliers, such as Aldrich Chemical Company and Arco Chemical Company and Alfa Chemical Company, and these reagents were not further purified in use unless otherwise specified. General reagents were purchased from Shantou Xilong Chemical Factory, Guangdong Guanghua Chemical Reagent Factory, Guangzhou Chemical Reagent Factory, Tianjin Haoyuyu Chemical Co., Ltd., Tianjin Fuchen Chemical Reagent Factory, Wuhan Xinhuayuan Technology Development Co., Ltd., Qingdao Tenglong Chemical Reagent Co., Ltd. and Qingdao Haiyang Chemical Factory.

A silica gel column was used as a chromatographic column. Silica gel (300-400 meshes) was purchased from Qingdao Haiyang Chemical Factory.

The measurement conditions of low resolution mass spectrometry (MS) data are: Agilent 6120 Quadrupoles HPLC-M (column model: Zorbax SB-C18, 2.1×30 mm, 3.5 microns, 6 min, flow rate 0.6 mL/min. Mobile phase: 5%-95% ($CH_3CN$ containing 0.1% formic acid ($H_2O$ containing 0.1% formic acid)), as detected by UV at 210 nm/254 nm using electrospray ionization (ESI).

Pure compounds were detected by UV at 210 nm/254 nm using Agilent 1260pre-HPLC or Calesep pump 250pre-HPLC (column model: NOVASEP 50/80 mm DAC).

Synthesis Example 1 (Compound 35)

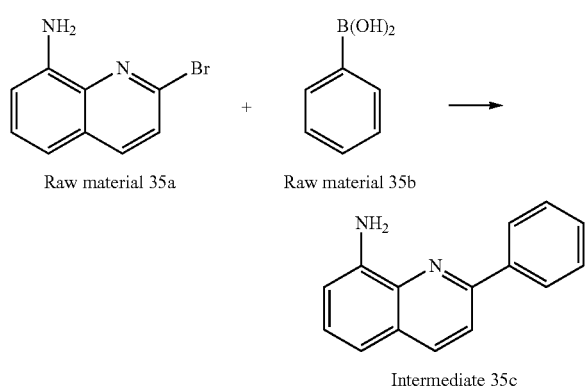

Raw material 35a    Raw material 35b

Intermediate 35c (1) Nitrogen gas (10 mL/min) was forced into a three-necked flask provided with a mechanical stirrer, a thermometer and an Allihn condenser for replacement for 15 min, and 0.40 mol of Raw material 35a, 0.48 mol of Raw material 35b, 0.80 mol of potassium carbonate, 0.04 mol of tetra-n-butylammonium bromide, 0.918 L of toluene, 0.230 L of absolute ethanol and 0.230 L of water were successively added. Stirring was initiated, the temperature was raised to 45~50° C., 0.0002 mol of tetrakis(triphenylphosphine) palladium was added into the flask, and heating was continued to reflux for a reaction at 62~65° C. for 4 h. The reaction solution was extracted with toluene, washed with water and passed through an insulated column with toluene at 60° C., the column passing solution was concentrated to a dry state, so that 0.24 mol of Intermediate 35c with a yield of 60% was obtained.

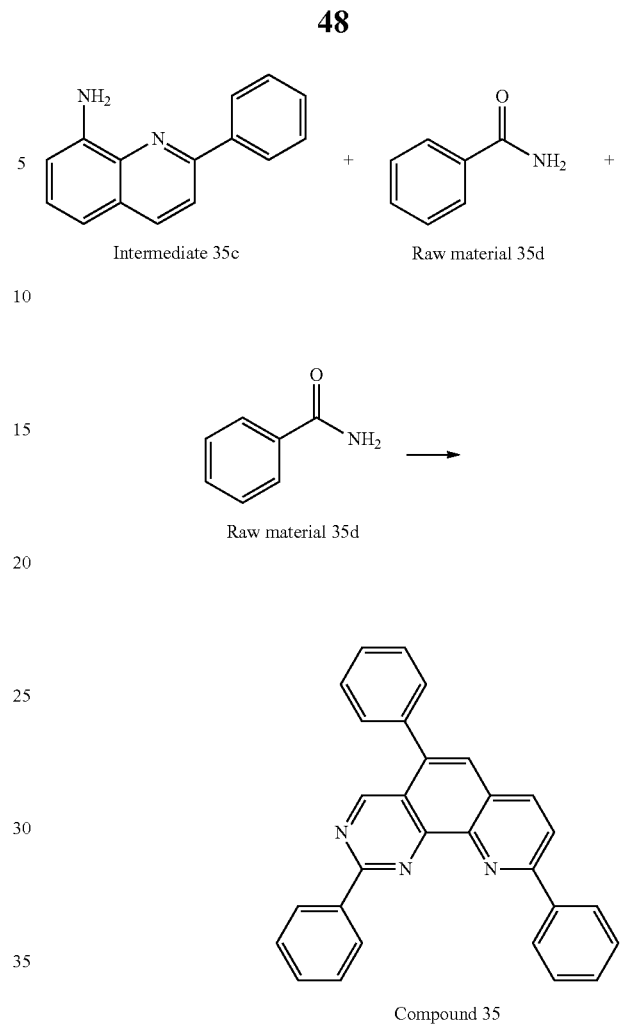

Intermediate 35c    Raw material 35d

Raw material 35d

Compound 35

0.30 mol of Intermediate 35c, 0.62 mol of Raw material 35d, 0.90 mol of phosphorus tribromide and 1.000 L of dichloromethane were added successively into a three-necked flask provided with a mechanical stirrer, a thermometer and an Allihn condenser; stirring was initiated, and the temperature was raised to 55~60° C. for a reaction for 2 h. 1.000 L of saturated aqueous solution of sodium bicarbonate was added into the reaction solution, stirred, kept still and dispensed, then dichloromethane was added into an aqueous phase, extracted and dispensed, a combined organic phase was washed with water twice, the organic phase was dried with anhydrous magnesium sulfate and passed through the column, the column passing solution was concentrated to a dry state, 30 ml of ethanol was added and filtered, so that 0.10 mol of Compound 35 with a yield of 33.12% was obtained. m/z=410.16[M+H]$^+$.

$^1$H-NMR (CDCl$_3$, 300 MHz) δ(ppm): 8.71 (d, 1H), 8.33-8.35 (m, 4H), 7.80-7.84 (m, 3H), 7.65 (m, 2H), 7.58 (d, 1H), 7.55-7.51 (m, 2H), 7.49-7.50 (m, 5H), 7.29 (d, 1H).

Synthesis Examples 2-16

The compounds in the following Table 1 were synthesized from Raw material 1 in Table 1 below instead of Raw material 35b in the same synthesis steps as the Compound 35 in synthesis example 1.

TABLE 1
| Synthesis Example No. | Raw material 1 | Compound Structure | Yield % | Mass spectrum (m/z) |
|---|---|---|---|---|
| 2 | 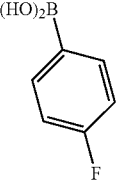 | 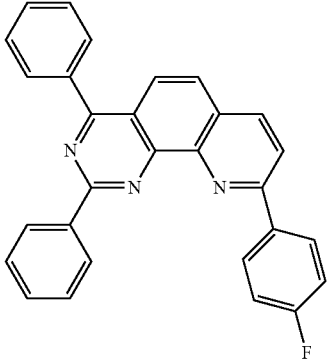<br>5 | 37.64 | 428.16 |
| 3 | 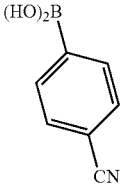 | 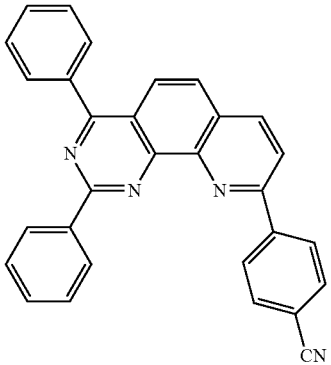<br>6 | 26.76 | 435.13 |
| 4 | | <br>7 | 39.13 | 486.20 |

TABLE 1-continued

| Synthesis Example No. | Raw material 1 | Compound Structure | Yield % | Mass spectrum (m/z) |
|---|---|---|---|---|
| 5 | (HO)₂B-(3,5-diphenylphenyl) | 8 | 37.89 | 562.22 |
| 6 | (HO)₂B-(3-biphenyl) | 9 | 43.71 | 486.20 |
| 7 | B(OH)₂-(4-(1-naphthyl)phenyl) | 11 | 27.69 | 536.20 |

TABLE 1-continued

| Synthesis Example No. | Raw material 1 | Compound Structure | Yield % | Mass spectrum (m/z) |
|---|---|---|---|---|
| 8 | | 12 | 34.12 | 536.22 |
| 9 | | 13 | 32.45 | 586.24 |
| 10 | | 14 | 30.42 | 586.71 |

TABLE 1-continued

| Synthesis Example No. | Raw material 1 | Compound Structure | Yield % | Mass spectrum (m/z) |
|---|---|---|---|---|
| 11 | (HO₂)B-dibenzofuran | 55 | 34.51 | 500.62 |
| 12 | (HO₂)B-dibenzothiophene | 56 | 31.03 | 516.76 |
| 13 | N-phenylcarbazole-Bpin | 57 | 26.7 | 499.60 |

TABLE 1-continued

| Synthesis Example No. | Raw material 1 | Compound Structure | Yield % | Mass spectrum (m/z) |
|---|---|---|---|---|
| 14 | (structure) | 58 | 36.8 | 675.72 |
| 15 | (structure) | 59 | 35.2 | 651.81 |
| 16 | (structure) | 60 | 30.1 | 651.82 |

TABLE 1-continued

| Synthesis Example No. | Raw material 1 | Compound Structure | Yield % | Mass spectrum (m/z) |
|---|---|---|---|---|
| 17 | [structure] | [structure] 61 | 29.4 | 625.83 |

Synthesis Example 18 (Compound 17)

[Intermediate 35c] + [Raw material 17a] + [Raw material 17b] → [Compound 17]

0.30 mol of Intermediate 35c, 0.31 mol of Raw material 17a, 0.31 mol of Raw material 17b, 0.90 mol of phosphorus tribromide and 1.000 L of dichloromethane were added successively into a three-necked flask provided with a mechanical stirrer, a thermometer and an Allihn condenser. Stirring was initiated, and the temperature was raised to 55~60° C. for a reaction for 2 h. 1.000 L of saturated solution of sodium bicarbonate was added into the reaction solution, dichloromethane was added, extracted and dispensed, an organic phase was dried with anhydrous magnesium sulfate and passed through the column at normal temperature, the column passing solution was concentrated to a dry state, so that 0.066 mol of Compound 17 with a yield of 22.12% was obtained. m/z=486.16[M+H]$^+$.

$^1$H-NMR (CDCl$_3$, 300 MHz) δ(ppm): 8.72 (d, 1H), 8.30-8.35 (m, 6H), 7.75-7.84 (m, 5H), 7.54-7.58 (m, 3H), 7.49-7.51 (m, 6H), 7.41 (m, 1H), 7.26 (d, 1H).

Synthesis Examples 19-20

The following compounds were synthesized from Raw material I in Table 2 below instead of Raw material 17a and Raw material II instead of Raw material 17b in the same synthesis steps as the Compound 17 in Synthesis example 17.

TABLE 2

| Synthesis Embodiment No. | Raw material I | Raw material II | Compound | Yield % | Mass spectrum (m/z) |
|---|---|---|---|---|---|
| 19 | benzamide | biphenyl-3-carboxamide | 18 | 24.98 | 486.19 |
| 20 | 4-phenylbenzamide | benzamide | 37 | 23.13 | 486.20 |

Synthesis Example 21 (Compound 62)

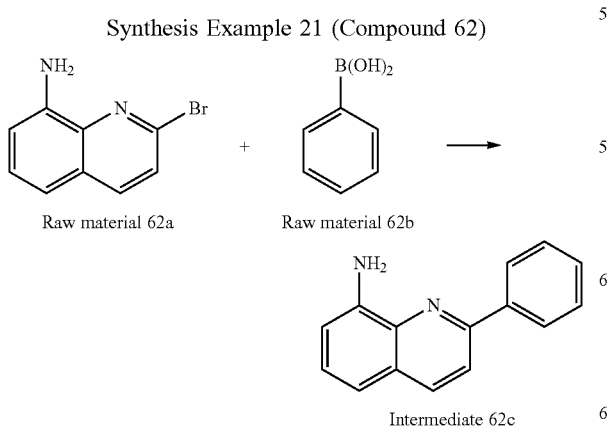

Raw material 62a + Raw material 62b → Intermediate 62c (1) Nitrogen gas (10 mL/min) was forced into a three-necked flask provided with a mechanical stirrer, a thermometer and an Allihn condenser for replacement for 15 min, and 0.40 mol of Raw material 62a, 0.48 mol of Raw material 62b, 0.80 mol of potassium carbonate, 0.04 mol of tetra-n-butylammonium bromide, 0.918 L of toluene, 0.230 L of absolute ethanol and 0.230 L of water were successively added. Stirring was initiated, the temperature was raised to 45~50° C., 0.0002 mol of tetrakis (triphenylphosphine) palladium was added into the flask, and heating was continued to reflux for a reaction at 62~65° C. for 4 h. The reaction solution was extracted with toluene, washed with water and passed through an insulated column with toluene at 60° C., the column passing solution was concentrated to a dry state, so that 0.40 mol of Intermediate 62c with a yield of 50% was obtained.

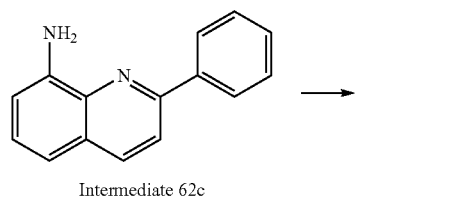

Intermediate 62c

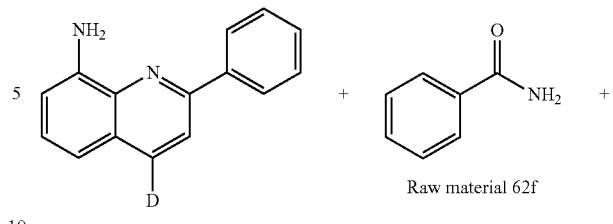

Intermediate 62e

Raw material 62f

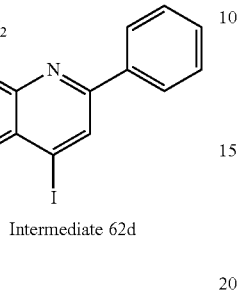

Intermediate 62d

Raw material 62f (2) Nitrogen gas (10 mL/min) was forced into a three-necked flask provided with a mechanical stirrer, a thermometer and an Allihn condenser for replacement for 15 min, 0.20 mol of raw material 62c and 100 ml of tetrahydrofuran were successively added, cooled to −35~40° C., 0.22 mol of TMP2Mg was added dropwise, the temperature was kept after dropping was completed, addition of 0.22 mol of tetrahydrofuran solution was started dropwise, and the temperature was kept for 1 h and gradually raised to room temperature for a reaction for 2 h. After the reaction was completed, 150 mL of water was added, so that a large amount of solid was separated out, 0.14 mol of Intermediate 62d with a yield of 70% was obtained after filtration and drying.

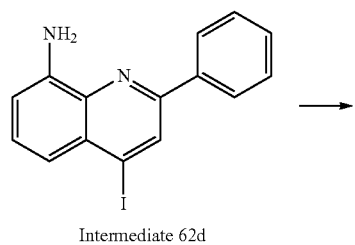

Intermediate 62d

Intermediate 62e

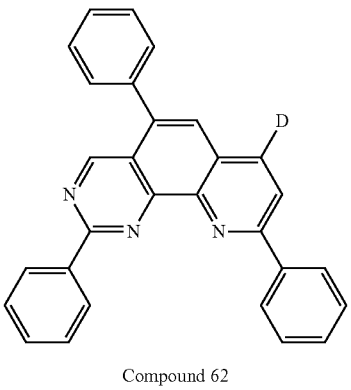

Compound 62

(3) Nitrogen gas (10 mL/min) was forced into a three-necked flask provided with a mechanical stirrer, a thermometer and an Allihn condenser for replacement for 15 min, 0.18 mol of Raw material 62e and 100 ml of ethanol were successively added, 0.01 g of Pd/C was added, and after D2 was forced into the flask, the flask was sealed for a reaction at 30~35° C. for 5 h. After the reaction was completed, 100 mL of water was added, so that a large amount of solid was separated out, 0.144 mol of Intermediate 62e with a yield of 80% was obtained after filtration and drying.

(4) 0.16 mol of Intermediate 62e, 0.4 mol of Raw material 62f, 0.5 mol of phosphorus tribromide and 200 mL of dichloromethane were added successively into a three-necked flask provided with a mechanical stirrer, a thermometer and an Allihn condenser; stirring was initiated, and the temperature was raised to 55~60° C. for a reaction at 55~60° C. for 2 h. 200 mL of saturated aqueous solution of sodium bicarbonate was added into the reaction solution, stirred, kept still and dispensed, then dichloromethane was added into an aqueous phase, extracted and dispensed, a combined organic phase was washed with water twice, the organic phase was dried with anhydrous magnesium sulfate and passed through the column, the column passing solution was concentrated to a dry state, 30 ml of ethanol was added and filtered, so that 0.10 mol of Compound 62 with a yield of 62.5% was obtained. m/z=411.16[M+H]$^+$.

$^1$H-NMR (CDCl$_3$, 300 MHz) δ(ppm): 8.70 (d, 1H), 8.33-8.35 (m, 4H), 7.81-7.84 (m, 3H), 7.65 (m, 2H), 7.58 (d, 1H), 7.55-7.51 (m, 2H), 7.49-7.51 (m, 4H), 7.26 (d, 1H).

The following compounds were synthesized from Raw material I in Table 3 below instead of Raw material 62b in the same synthesis steps as Compound 62 in Synthesis example 21.

TABLE 3

| Synthesis Embodiment No. | Raw material I | Compound Structure | Yield % | Mass spectrum (m/z) |
|---|---|---|---|---|
| 22 | (HO₂)B-[biphenyl] | Compound 63 | 19.13 | 487.20 |
| 23 | (HO₂)B-[m-terphenyl] | Compound 64 | 17.81 | 564.22 |
| 24 | B(OH)₂-[phenyl-naphthyl] | Compound 65 | 18.60 | 537.50 |

TABLE 3-continued

| Synthesis Embodiment No. | Raw material I | Compound Structure | Yield % | Mass spectrum (m/z) |
|---|---|---|---|---|
| 25 | | 66 | 22.41 | 587.71 |
| 26 | | 67 | 26.18 | 676.69 |

TABLE 3-continued

| Synthesis Embodiment No. | Raw material I | Compound Structure | Yield % | Mass spectrum (m/z) |
|---|---|---|---|---|
| 27 | (structure 68 raw material) | (structure 68) | 15.20 | 652.81 |
| 28 | (structure 69 raw material) | (structure 69) | 20.12 | 652.79 |
| 29 | (structure 70 raw material) | (structure 70) | 19.32 | 626.78 |

The following Application examples 1 to 29 are used to illustrate the use of the electron transport compound of the present disclosure in the electron transport layer in the organic electroluminescent device.

Application Example 1

A manufacturing method of organic light-emitting devices, comprising the following steps:

(1) Firstly, a glass substrate with 1500 Å indium tin oxide (ITO) electrodes was ultrasonically cleaned with distilled water and methanol successively, and dried;

(2) Secondly, the glass substrate was cleaned with oxygen plasma for 5 minutes, and then the cleaned anode substrate was loaded into vacuum deposition equipment;

(3) A compound 2-TNATA (CAS: 185690-41-9) was vacuum deposited on the ITO electrode to form a hole injection layer HIL with a thickness of 500 Å, then NPB (N,N'-diphenyl-N,N'-di-(1-naphthyl)-1,1'-biphenyl-4,4'-diamine) was vacuum deposited on the hole injection layer, so that a hole transport layer HTL with a thickness of 600 Å was formed, and TCTA (its structure is as follows) was vapor deposited on the hole transport layer, so that an electron-blocking layer EBL with a thickness of 200 Å was formed. Then, a host light-emitting material BPO (its structure is as follows) and a dopant EM (its structure is as follows) were codeposited onto the hole transport area at a mass ratio of 96:4, so that a light-emitting layer EML with a thickness of 300 Å was formed;

(4) A hole-blocking layer DPVBi (CAS: 142289-08-5) with a thickness of 200 Å was vacuum deposited on the light-emitting layer, so that a hole-blocking layer was formed;

(5) A compound 35 was vacuum deposited on the hole-blocking layer, so that an electron transport layer with a thickness of 300 Å was formed, LiQ (8-hydroxyquinoline lithium) was vapor deposited on the electron transport layer to form an electron injection layer EIL with a thickness of 15 Å, then magnesium (Mg) and silver (Ag) were mixed at a deposition rate of 1:9 and vacuum deposited on the electron injection layer to form a cathode with a thickness of 120 Å. In addition, N-(4-(9H-carbazole-9-yl)phenyl)-4'-(9H-carbazole-9-yl)-N-phenyl-[1,1'-biphenyl]-4-amine with a thickness of 650 Å was vapor deposited on the above cathode to form an organic capping layer (CPL), thus the organic light-emitting device was manufactured, and the prepared organic light-emitting device was recorded as A1.

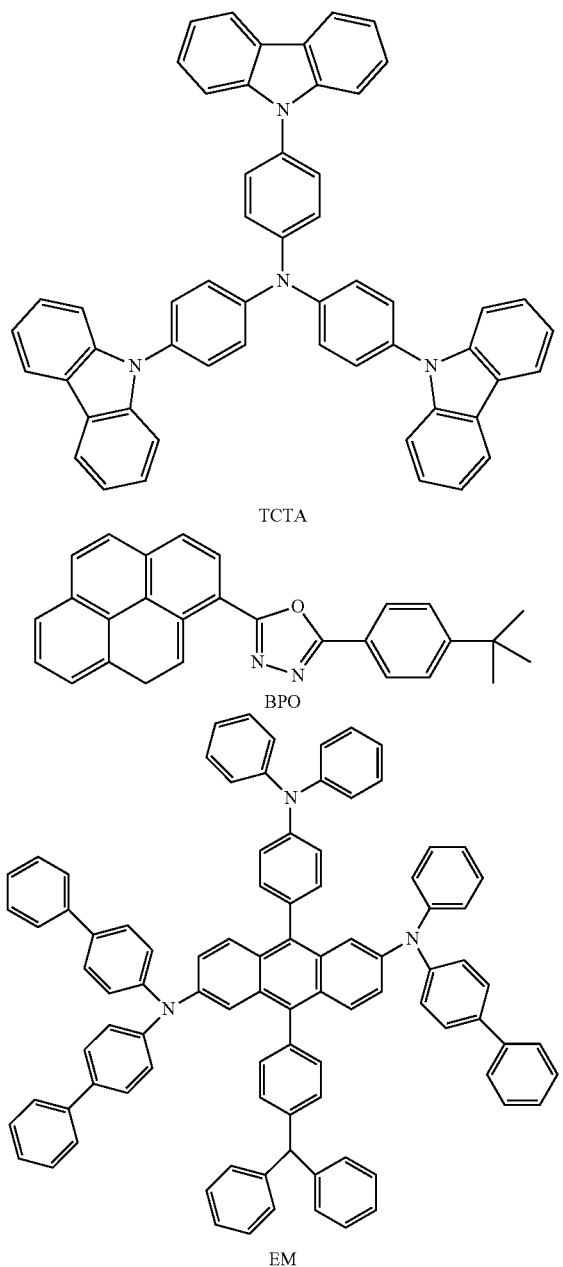

Application Example 2 to Application Example 29

The organic electroluminescent devices were manufactured by the same method as Application Example 1, and the difference was that the organic electroluminescent devices 2 to 29 were manufactured from Compound 5, Compound 6, Compound 7, Compound 8, Compound 9, Compound 11, Compound 12, Compound 13, Compound 17, Compound 18, Compound 37, Compound 14, Compound 55, Compound 56, Compound 57, Compound 58, Compound 59, Compound 60, Compound 61, Compound 62, Compound 63, Compound 64, Compound 65, Compound 66, Compound 67, Compound 68, Compound 69 and Compound 70 instead of Compound 35 as electron transport layers respectively in Application Examples 2 to 29.

Comparative Example 1

In Comparative Example 1, the organic electroluminescent device was manufactured by the same method as Application Example 1, and the only difference was that: $Alq_3$ (its structure is as follows) was used instead of Compound 35 of Application Example 1 as the electron transport layer material, thus obtaining the organic electroluminescent device D1.

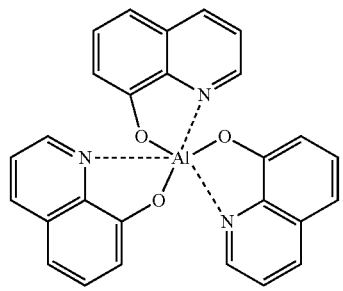

Comparative Example 2

In Comparative example 2, the organic electroluminescent device was manufactured by the same method as Application example 1, and the only difference was that: Compound A (its structure is as follows) was used instead of Compound 35 of Application example 1 as the electron transport layer, thus obtaining the organic electroluminescent device D2.

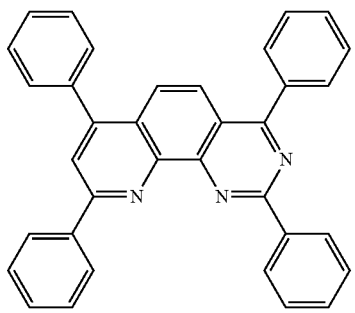

A

Comparative Example 3

In Comparative example 3, the organic electroluminescent device was manufactured by the same method as Application example 1, and the only difference was that: Compound B (its structure is as follows) was used instead of Compound 35 of Application example 1 as the electron transport layer, thus obtaining the organic electroluminescent device D3.

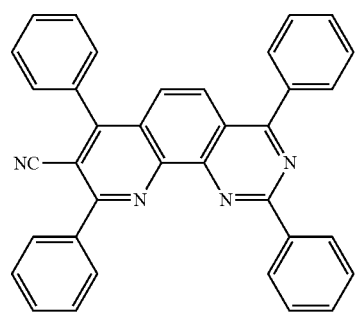

B

For the obtained organic electroluminescent devices 1 to 29 and Comparative Example 1 to 3 as mentioned above, the T95 device lifetime was tested at 15 $mA/cm^2$, and the data of voltage, efficiency and chromaticity coordinates was tested at the constant current density of 10 $mA/cm^2$. The results are shown in Table 4.

TABLE 4

List of Electron Light-emitting Characteristics of Organic Electroluminescent Devices 1 to 29 and Comparative Example 1 to 3

| No. | Electron transport material | Driving voltage (V) | Luminous efficiency (Cd/A) | External quantum efficiency (EQE) | Chromaticity coordinates (CIEy) | T95(h) |
|---|---|---|---|---|---|---|
| Application Example 1 | Compound 35 | 4.1 | 6.1 | 12.3 | 0.050 | 168 |
| Application Example 2 | Compound 5 | 4.0 | 6.5 | 12.0 | 0.053 | 159 |
| Application Example 3 | Compound 6 | 3.8 | 6.8 | 13.3 | 0.052 | 175 |
| Application Example 4 | Compound 7 | 4.0 | 6.8 | 13.0 | 0.050 | 182 |
| Application Example 5 | Compound 8 | 3.8 | 6.9 | 12.8 | 0.053 | 163 |
| Application Example 6 | Compound 9 | 3.9 | 6.3 | 12.5 | 0.051 | 168 |
| Application Example 7 | Compound 11 | 4.1 | 6.0 | 11.8 | 0.054 | 169 |
| Application Example 8 | Compound 12 | 4.0 | 6.8 | 13.3 | 0.052 | 163 |
| Application Example 9 | Compound 13 | 3.8 | 6.4 | 12.6 | 0.053 | 168 |
| Application Example 10 | Compound 17 | 3.9 | 6.3 | 11.9 | 0.052 | 185 |
| Application Example 11 | Compound 18 | 3.9 | 6.1 | 12.1 | 0.053 | 175 |

TABLE 4-continued

List of Electron Light-emitting Characteristics of Organic Electroluminescent Devices 1 to 29 and Comparative Example 1 to 3

| No. | Electron transport material | Driving voltage (V) | Luminous efficiency (Cd/A) | External quantum efficiency (EQE) | Chromaticity coordinates (CIEy) | T95(h) |
|---|---|---|---|---|---|---|
| Application Example 12 | Compound 37 | 4.0 | 6.0 | 12.0 | 0.051 | 168 |
| Application Example 13 | Compound 14 | 4.1 | 5.7 | 12.3 | 0.052 | 157 |
| Application Example 14 | Compound 55 | 3.9 | 6.8 | 13.1 | 0.050 | 173 |
| Application Example 15 | Compound 56 | 4.0 | 5.9 | 12.6 | 0.053 | 162 |
| Application Example 16 | Compound 57 | 4.1 | 6.4 | 12.9 | 0.051 | 167 |
| Application Example 17 | Compound 58 | 4.1 | 5.7 | 11.3 | 0.052 | 159 |
| Application Example 18 | Compound 59 | 4.0 | 6.0 | 12.0 | 0.050 | 163 |
| Application Example 19 | Compound 60 | 3.9 | 5.9 | 11.8 | 0.051 | 160 |
| Application Example 20 | Compound 61 | 3.8 | 6.1 | 12.0 | 0.050 | 167 |
| Application Example 21 | Compound 62 | 4.1 | 6.0 | 12.1 | 0.051 | 152 |
| Application Example 22 | Compound 63 | 3.9 | 6.6 | 13.0 | 0.051 | 186 |
| Application Example 23 | Compound 64 | 3.8 | 5.8 | 12.6 | 0.050 | 162 |
| Application Example 24 | Compound 65 | 4.0 | 6.4 | 12.9 | 0.049 | 157 |
| Application Example 25 | Compound 66 | 4.2 | 5.6 | 11.7 | 0.051 | 151 |
| Application Example 26 | Compound 67 | 3.9 | 5.8 | 12.4 | 0.050 | 157 |
| Application Example 27 | Compound 68 | 4.0 | 5.7 | 10.9 | 0.053 | 154 |
| Application Example 28 | Compound 69 | 4.1 | 5.9 | 11.4 | 0.052 | 162 |
| Application Example 29 | Compound 70 | 3.9 | 6.0 | 12.3 | 0.051 | 161 |
| Comparative Example 1 | $Alq_3$ | 4.4 | 5.4 | 10.2 | 0.051 | 143 |
| Comparative Example 2 | Compound A | 4.7 | 4.1 | 8.2 | 0.053 | 122 |
| Comparative Example 3 | Compound B | 4.5 | 5.0 | 9.8 | 0.050 | 131 |

It can be seen from the above results that when the electron transport compound of the present disclosure as an electron transport material is compared with Comparative Example 1 using the well-known electron transport material $Alq_3$, Comparative Example 2 using compound A and Comparative Example 3 using compound B: the driving voltage of the organic electroluminescent devices 1 to 29 prepared in Application Examples 1 to 29 was 3.8~4.2V, reduced by at least 4.5% compared to the driving voltage (4.4V) of Comparative Example 1, reduced by at least 10.600 compared to the driving voltage (4.7V) of Comparative Example 2, and reduced by at least 6.700 compared to the driving voltage (4.5V) of Comparative Example 3. The luminous efficiency of the organic electroluminescent devices 1 to 29 was 5.7~6.9 Cd/A, increased by at least 5.6% compared to the luminous efficiency (5.4 Cd/A) of Comparative Example 1, increased by at least 390% compared to the luminous efficiency (4.1 Cd/A) of Comparative Example 2, and increased by at least 140% compared to the luminous efficiency (5.0 Cd/A) of Comparative Example 3. The external quantum efficiency of 1 to 29 was 10.9%~13.3%, increased by at least 6.9% compared to the external quantum efficiency (10.2%) of Comparative Example 1, increased by at least 33% compared to the external quantum efficiency (8.2%) of Comparative Example 2, and increased by at least 11.22% compared to the external quantum efficiency (9.8%) of Comparative Example 3. The T95 lifetime of the organic electroluminescent devices 1 to 29 was 152~186 h, increased by at least 6.3% compared to the T95 lifetime (143 h) of Comparative Example 1, increased by at least 24.6% compared to the T95 lifetime (122 h) of Comparative Example 2, and increased by at least 16% compared to the T95 lifetime (131 h) of Comparative Example 3.

It is thus clear that the organic electroluminescent devices prepared in the Application Examples 1 to 29 have lower driving voltage, higher luminous efficiency and higher external quantum efficiency compared to the Comparative Examples 1-3. As the material of the electron transport layer, the electron transport compound of the present disclosure has better luminous efficiency, better electrical stability and longer lifetime than the Comparative Examples, and can significantly improve the performance of the organic electroluminescent device when used in the electron transport layer of the organic electroluminescent device. In addition, the compound of the present disclosure is significantly improved in driving voltage, luminous efficiency, external quantum efficiency and lifetime performance compared to the compounds with aryl as R in Comparative Examples 2 and 3.

The preferred embodiments of the present disclosure are described in detail above in combination with the drawings. However, the present disclosure is not limited to the specific details in the above embodiments, various simple variants may be created for the technical solution of the present disclosure within the scope of technical conception of the present disclosure, and all these simple variants belong to the protection scope of the present disclosure.

In addition, it should be noted that the specific technical features described in the above specific embodiments can be combined in any suitable way without contradiction, and various possible combination modes will not be otherwise specified in the present disclosure in order to avoid unnecessary repetition.

Moreover, various embodiments of the present disclosure can also be combined arbitrarily, and should be considered as the contents disclosed by the present disclosure as long as they do not violate the idea of the present disclosure.

The invention claimed is:

1. A nitrogen-containing organic compound having a structure represented by formula (1):

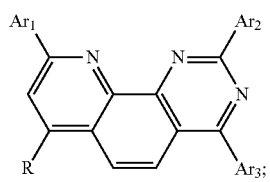

Formula (1)

wherein R is hydrogen or deuterium;

Ar₁, Ar₂ and Ar₃ are the same or different, and are each independently selected from a group consisting of the following groups:

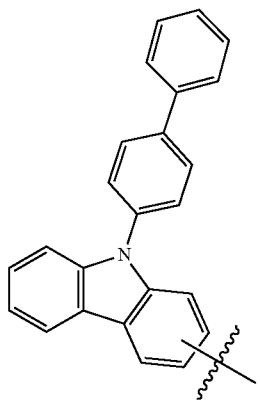

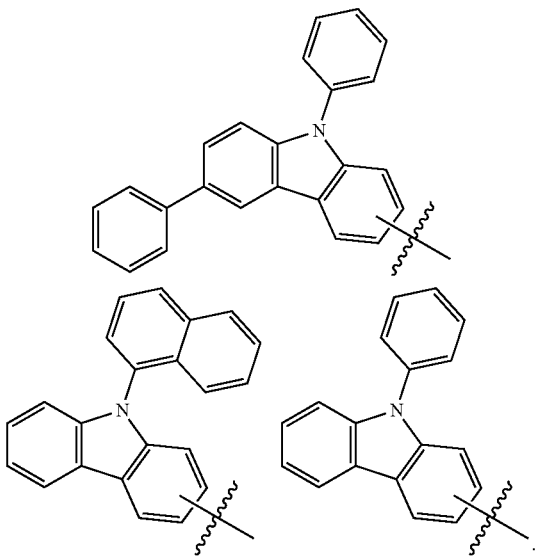

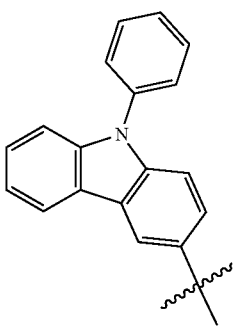

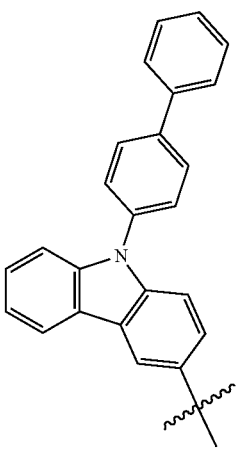

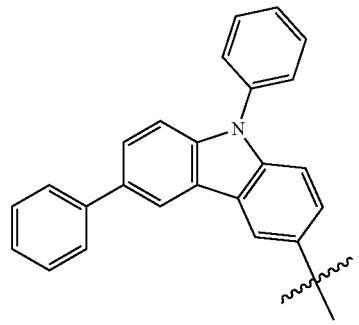

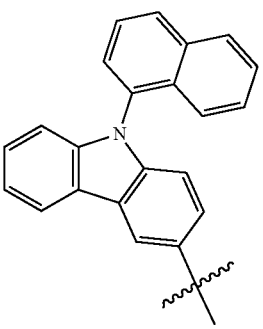
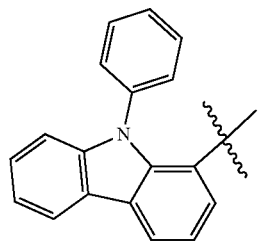

2. The nitrogen-containing organic compound according to claim 1, wherein the Ar₁, Ar₂ and Ar₃ are the same or different, and are independently selected from a group consisting of the following groups:

3. An organic electroluminescent device, comprising the nitrogen-containing organic compound according to claim 1.

4. The use organic electroluminescent device according to claim 3, wherein the nitrogen-containing organic compound is used as an electron transport layer material of the organic electroluminescent device.

5. An organic electroluminescent device, comprising an anode, a cathode, and at least one functional layer between the anode and the cathode, wherein the functional layer comprises a hole injection layer, a hole transport layer, an organic electroluminescent layer, an electron transport layer and an electron injection layer, wherein the electron transport layer contains the nitrogen-containing organic compound according to claim 1.

* * * * *